(12) United States Patent
Hsu et al.

(10) Patent No.: US 7,062,316 B2
(45) Date of Patent: Jun. 13, 2006

(54) CROSS CHAMBER INTERVAL CORRELATION

(75) Inventors: William Hsu, Circle Pines, MN (US); Robert J. Sweeney, Woodbury, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 73 days.

(21) Appl. No.: 10/347,725

(22) Filed: Jan. 21, 2003

(65) Prior Publication Data

US 2003/0109792 A1 Jun. 12, 2003

Related U.S. Application Data

(60) Continuation of application No. 09/615,014, filed on Jul. 12, 2000, now Pat. No. 6,522,917, which is a division of application No. 09/283,159, filed on Apr. 1, 1999, now Pat. No. 6,179,865.

(51) Int. Cl.
*A61B 5/0402* (2006.01)

(52) U.S. Cl. .................................................. 600/518
(58) Field of Classification Search ............... 600/372, 600/373, 374, 508, 509, 515, 516, 518, 519, 600/521; 607/4, 5, 9, 14, 119
See application file for complete search history.

(56) References Cited

U.S. PATENT DOCUMENTS

| | | | | |
|---|---|---|---|---|
| 4,515,161 A | 5/1985 | Wittkampf et al. | .......... | 128/419 |
| 4,543,963 A | 10/1985 | Gessman | .................... | 128/702 |
| 4,572,192 A | 2/1986 | Jackman et al. | ...... | 128/419 PG |
| 4,577,634 A | 3/1986 | Gessman | .............. | 128/419 PG |

(Continued)

FOREIGN PATENT DOCUMENTS

EP  0033418  8/1981

(Continued)

OTHER PUBLICATIONS

Hsu, William.,et al., U.S. Appl. No. 09/417,588, entitled System and Method for Classifying Tachycardia Arrhythmias Having 1:1 Atrial to Ventricular Rhythms, filed on Oct. 13, 1999.

(Continued)

*Primary Examiner*—Robert E. Pezzuto
*Assistant Examiner*—Frances P. Oropeza
(74) *Attorney, Agent, or Firm*—Schwegman, Lundberg, Woessner & Kluth, P.A.

(57) ABSTRACT

A system and method for discriminating cardiac rhythms occurring in an antegrade direction from cardiac rhythms occurring in a retrograde direction. Atrial and ventricular contractions are sensed, from which atrial and ventricular cycle lengths are determined. Ventricular contractions are also analyzed to determine the occurrence of a tachycardia episode that has a one-to-one association of atrial contractions to ventricular contractions. During a tachycardia episode having a one-to-one association of atrial contractions to ventricular contractions, the atrial cycle lengths are paired with the ventricular cycle lengths, where for each of the atrial cycle lengths the atrial cycle length is paired with at least one ventricular cycle length started before the first atrial contraction of each of the atrial cycle lengths and paired with at least one ventricular cycle length started after the first atrial contraction of each of the atrial cycle lengths. A retrograde correlation coefficient is then determined for the atrial cycle lengths paired with the ventricular cycle lengths started before the first atrial contraction, and an antegrade correlation coefficient is determined for the atrial cycle lengths paired with the ventricular cycle lengths started after the first atrial contraction. The tachycardiac episode is then classified based on a comparison of the antegrade correlation coefficient and the retrograde correlation coefficient.

34 Claims, 13 Drawing Sheets

U.S. PATENT DOCUMENTS

| | | | |
|---|---|---|---|
| 4,583,553 A | 4/1986 | Shah et al. ................. 128/704 |
| 4,721,114 A | 1/1988 | DuFault et al. ............. 128/696 |
| 4,802,483 A | 2/1989 | Lindgren ............. 128/419 PG |
| 4,860,749 A | 8/1989 | Lehmann ............. 128/419 PG |
| 4,917,115 A | 4/1990 | Flammang et al. ... 128/419 PG |
| 4,928,688 A | 5/1990 | Mower ................. 128/419 PG |
| 4,998,974 A | 3/1991 | Aker ..................... 128/419 PG |
| 5,000,189 A | 3/1991 | Throne et al. .............. 128/702 |
| 5,014,284 A | 5/1991 | Langer et al. ................. 375/30 |
| 5,014,698 A | 5/1991 | Cohen ......................... 128/419 |
| 5,020,540 A | 6/1991 | Cahmoun .................... 128/696 |
| 5,107,850 A | 4/1992 | Olive .......................... 128/705 |
| 5,129,394 A | 7/1992 | Mehra ................. 128/419 PG |
| 5,156,148 A | 10/1992 | Cohen ................. 128/419 PG |
| 5,183,040 A | 2/1993 | Nappholz et al. ..... 128/419 PG |
| 5,184,615 A | 2/1993 | Nappholz et al. ..... 128/419 PG |
| 5,193,550 A | 3/1993 | Duffin ......................... 129/697 |
| 5,215,098 A | 6/1993 | Steinhaus et al. ........... 128/702 |
| 5,217,021 A | 6/1993 | Steinhaus et al. ........... 128/702 |
| 5,228,438 A | 7/1993 | Buchanan ............. 128/419 PG |
| 5,240,009 A | 8/1993 | Williams ..................... 128/702 |
| 5,243,980 A | 9/1993 | Mehra ........................... 607/6 |
| 5,247,021 A | 9/1993 | Fujisawa et al. ............. 525/254 |
| 5,253,644 A | 10/1993 | Elmvist ......................... 607/14 |
| 5,255,186 A | 10/1993 | Steinhaus et al. ........... 364/413 |
| 5,273,049 A | 12/1993 | Steinhaus et al. ........... 128/696 |
| 5,275,621 A | 1/1994 | Mehra ........................... 607/5 |
| 5,280,792 A | 1/1994 | Leong et al. ................ 128/702 |
| 5,311,874 A | 5/1994 | Baumann et al. ........... 128/705 |
| 5,327,900 A | 7/1994 | Mason et al. ................ 128/705 |
| 5,334,220 A | 8/1994 | Sholder .......................... 607/9 |
| 5,350,406 A | 9/1994 | Nitzsche et al. .............. 607/14 |
| 5,351,696 A | 10/1994 | Riff et al. .................... 128/702 |
| 5,360,436 A | 11/1994 | Alt et al. ....................... 607/18 |
| 5,365,932 A | 11/1994 | Greenhut ..................... 128/696 |
| 5,366,487 A | 11/1994 | Adams et al. ................. 607/5 |
| 5,370,125 A | 12/1994 | Mason et al. ................ 128/705 |
| 5,383,910 A * | 1/1995 | den Dulk ...................... 607/14 |
| 5,400,795 A | 3/1995 | Murphy et al. ............. 128/702 |
| 5,417,714 A | 5/1995 | Levine et al. .................. 607/9 |
| 5,447,519 A | 9/1995 | Peterson ......................... 607/5 |
| 5,447,524 A | 9/1995 | Alt ............................... 607/19 |
| 5,456,261 A | 10/1995 | Luczyk ....................... 128/702 |
| 5,462,060 A | 10/1995 | Jacobson et al. ........... 128/702 |
| 5,476,482 A | 12/1995 | Lu ................................. 607/9 |
| 5,496,350 A | 3/1996 | Lu ............................... 607/14 |
| 5,509,927 A | 4/1996 | Epstein et al. ................ 607/32 |
| 5,542,430 A | 8/1996 | Farrugia et al. ............. 128/705 |
| 5,551,427 A | 9/1996 | Altman ....................... 128/642 |
| 5,560,369 A | 10/1996 | McClure et al. ............ 128/704 |
| 5,626,623 A | 5/1997 | Kieval et al. .................. 607/23 |
| 5,634,468 A | 6/1997 | Platt et al. ................... 128/696 |
| 5,645,070 A | 7/1997 | Turcott ....................... 128/702 |
| 5,687,737 A | 11/1997 | Branham et al. ........... 128/710 |
| 5,690,689 A | 11/1997 | Sholder ........................ 607/24 |
| 5,697,377 A | 12/1997 | Witkampf ................... 128/696 |
| 5,700,283 A | 12/1997 | Salo ............................. 607/17 |
| 5,712,801 A | 1/1998 | Turcott ....................... 364/550 |
| 5,713,930 A | 2/1998 | van der Veen et al. ....... 607/25 |
| 5,713,932 A | 2/1998 | Gillberg et al. ............... 607/27 |
| 5,730,141 A | 3/1998 | Fain et al. ................... 128/705 |
| 5,738,096 A | 4/1998 | Ben-Haim ............... 128/653.1 |
| 5,738,105 A | 4/1998 | Kroll ............................ 128/708 |
| 5,741,308 A | 4/1998 | Sholder ......................... 607/9 |
| 5,749,906 A | 5/1998 | Kieval et al. .................. 607/9 |
| 5,755,736 A | 5/1998 | Gillberg et al. ................ 607/4 |
| 5,772,604 A | 6/1998 | Langberg et al. ........... 600/518 |
| 5,776,072 A * | 7/1998 | Hsu et al. ................... 600/518 |
| 5,776,167 A | 7/1998 | Levine et al. .................. 607/9 |
| 5,779,645 A | 7/1998 | Olson et al. ................ 600/518 |
| 5,788,717 A | 8/1998 | Mann et al. ................... 607/14 |
| 5,797,399 A | 8/1998 | Morris et al. ............... 128/705 |
| 5,800,464 A | 9/1998 | Kieval ............................ 607/9 |
| 5,800,471 A | 9/1998 | Baumann ..................... 607/25 |
| 5,810,739 A | 9/1998 | Bornzin et al. ............. 600/510 |
| 5,814,077 A | 9/1998 | Sholder et al. ................. 607/9 |
| 5,836,987 A | 11/1998 | Baumann et al. ............. 607/17 |
| 5,848,972 A | 12/1998 | Triedman et al. ........... 600/508 |
| 5,857,977 A | 1/1999 | Caswell et al. ............. 600/518 |
| 5,858,977 A | 1/1999 | Aukerman et al. ........... 514/12 |
| 5,861,007 A | 1/1999 | Hess et al. ...................... 607/9 |
| 5,873,895 A | 2/1999 | Sholder et al. ................. 607/9 |
| 5,873,897 A | 2/1999 | Armstrong et al. ........... 607/14 |
| 5,885,221 A | 3/1999 | Hsu et al. .................... 600/515 |
| 5,897,575 A | 4/1999 | Wickham ...................... 607/4 |
| 5,935,081 A | 8/1999 | Kadhiresan ................. 600/513 |
| 5,944,744 A | 8/1999 | Paul et al. ...................... 607/9 |
| 5,978,700 A | 11/1999 | Nigam ........................ 600/518 |
| 5,978,710 A | 11/1999 | Prutchi et al. ................ 607/17 |
| 5,983,126 A | 11/1999 | Wittkampf ................. 600/509 |
| 5,983,138 A | 11/1999 | Kramer ......................... 607/9 |
| 6,026,320 A | 2/2000 | Carlson et al. ............. 600/510 |
| 6,044,298 A | 3/2000 | Salo et al. .................... 607/17 |
| 6,049,735 A | 4/2000 | Hartley et al. ................. 607/9 |
| 6,052,620 A | 4/2000 | Gillberg et al. ................ 607/4 |
| 6,081,747 A | 6/2000 | Levine et al. .................. 607/9 |
| 6,179,865 B1 | 1/2001 | Hsu et al. .................... 607/518 |
| 6,246,909 B1 | 6/2001 | Ekwall .......................... 607/9 |
| 6,522,917 B1 | 2/2003 | Hsu et al. .................... 600/518 |

FOREIGN PATENT DOCUMENTS

| | | |
|---|---|---|
| EP | 0469817 | 2/1992 |
| EP | 0506230 | 9/1992 |
| EP | 0540141 | 5/1993 |
| EP | 0 879 621 A2 * | 5/1998 |
| EP | 0879621 | 11/1998 |
| WO | WO-97/39681 | 4/1996 |
| WO | WO-97/39799 | 10/1997 |
| WO | WO-98/53879 | 12/1998 |

OTHER PUBLICATIONS

Lecarpentier, G. L.,et al. ,"Differentiation of sinus tachycardia from ventricular tachycardia with 1:1 ventriculoatrial conduction in dual chamber implantable cardioverter defibrillators: feasibility of a criterion based on atrioventricular interval.", *PACE 1994; 17(Pt. I),* (1994), 1818–1831.

Thompson, J.A.,et al. ,"Ventriculoatrial conduction metrics for classification of ventricular tachycardia with 1:1 retrograde conduction with dual–chamber sensing implantable cardioverter defibrillators", *J. of Electrocardiography 1998; 31,* (1998), 152–156.

Thompson, Julie, "Template based AV/VA interval comparison for the discrimination of cardiac arrhythmia" *Application Ser. No. 10/844,475 filed May 12, 2004, Attorney Docket No. 279.717US1,* 33 pgs.

* cited by examiner

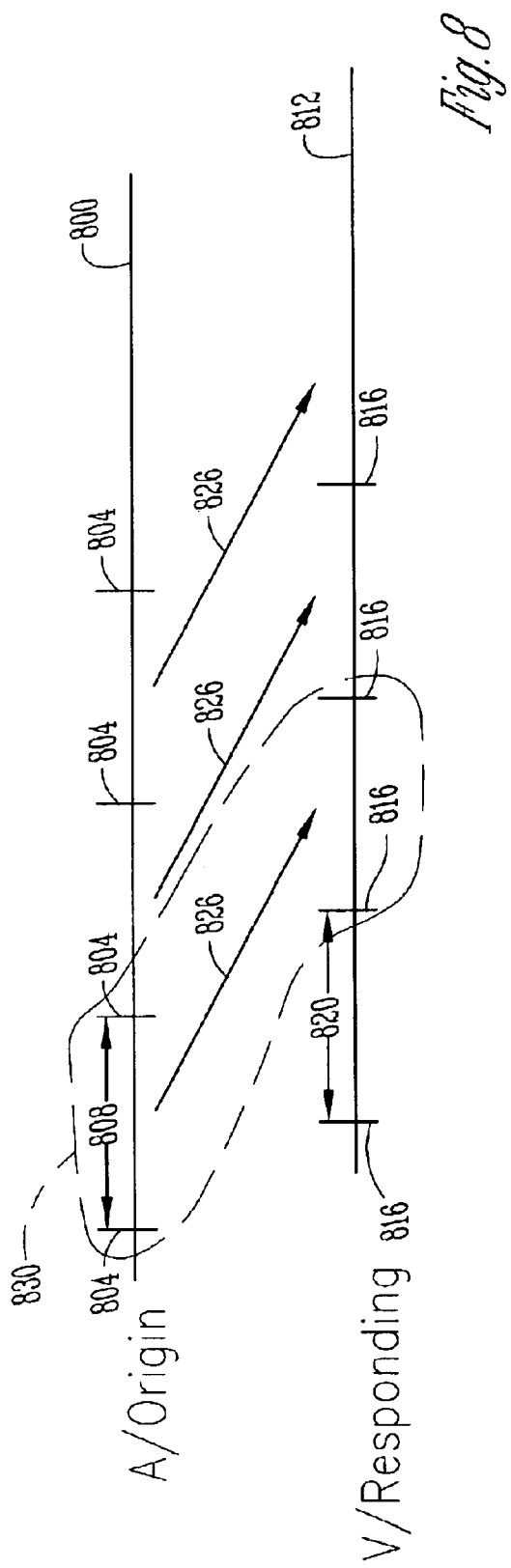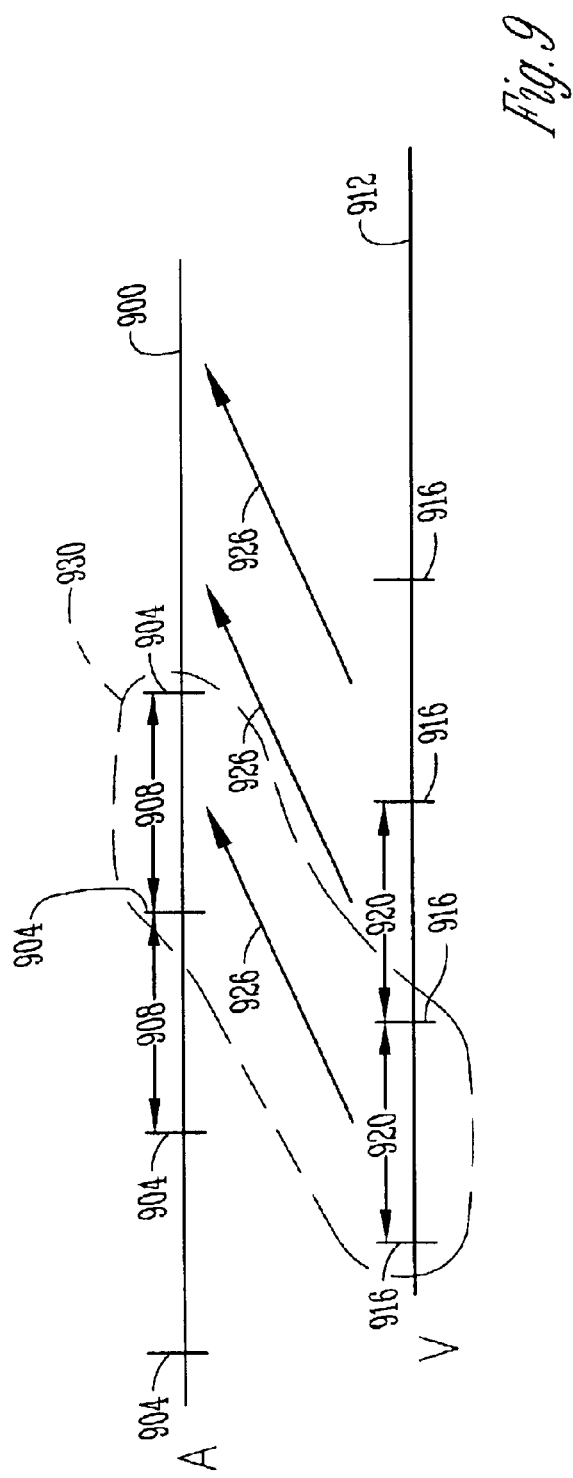

CROSS CHAMBER INTERVAL CORRELATION

CROSS REFERENCE TO RELATED APPLICATIONS

This application is a continuation of U.S. application Ser. No. 09/615,014, filed on Jul. 12, 2000, now U.S. Pat. NO 6,522,917, which is a division of U.S. application Ser. No. 09/283,159, filed on Apr. 1, 1999, now issued as U.S. Pat. No. 6,179,865, the specifications of which are hereby incorporated by reference.

FIELD OF THE INVENTION

The present invention relates generally to implantable medical devices and more particularly to a system and method for discriminating cardiac rhythms occurring in an antegrade direction from cardiac rhythms occurring in a retrograde direction.

BACKGROUND

The heart is generally divided into two chambers, the atrial chamber and the ventricular chamber. As the heart beats, the atrial chamber and the ventricular chamber of the heart go through a cardiac cycle. The cardiac cycle consists of one complete sequence of contraction and relaxation of the chambers of the heart. The terms systole and diastole are used to describe the contraction and relaxation phases the chambers of the heart experience during a cardiac cycle. In systole, the ventricular muscle cells are contracting to pump blood through the circulatory system. During diastole, the ventricular muscle cells relax, causing blood from the atrial chamber to fill the ventricular chamber. After the period of diastolic filling, the systolic phase of a new cardiac cycle is initiated.

Control over the timing and order of the atrial and ventricular contractions during the cardiac cycle is critical for the heart to pump blood efficiently. Efficient pumping action of the heart requires precise coordination of the contraction of individual cardiac muscle cells. Contraction of each cell is triggered when an electrical excitatory impulse (an "action potential") sweeps over the heart. Proper coordination of the contractual activity of the individual cardiac muscle cells is achieved primarily by the conduction of the action potential from one cell to the next by gap junctions that connect all cells of the heart into a functional system. In addition, muscle cells in certain areas of the heart are specifically adapted to control the frequency of cardiac excitation, the pathway of conduction and the rate of impulse propagation through various regions of the heart. The major components of this specialized excitation and conduction system include the sinoatrial node (SA node), the atrioventricular node (AV node), the bundle of His, and specialized cells called Purkinje fibers.

The SA node is located at the junction of the superior vena cava and the right atrium. Specialized atrium muscle cells of the SA node spontaneously generate action potentials which are then propagated through the rest of the heart to cause cardiac contraction. This SA node region normally acts as the intrinsic cardiac pacemaker. The action potential generated by the SA node spreads through the atrial wall, causing the atrial chambers to contract and the P-wave of an electrocardiogram signal.

The AV node consists of small, specialized cells located in the lower portion of the atrial chamber. The AV node acts like a bridge for the action potential to cross over into the ventricular chamber of the heart. Once the action potential has crossed over to the ventricular chambers, the bundle of His carries the action potential to specialized cardiac fibers called Purkinje fibers. The Purkinje fibers then distribute the action potential throughout the ventricular chamber of the heart. This results in rapid, very nearly simultaneous excitation of all ventricular muscle cells. The conduction of the action potential through the AV node and into the ventricular chambers creates the QRS-complex of an electrogram signal.

During the cardiac cycle, the action potential moves in an antegrade direction, first causing the atrial chambers to contract and then causing the ventricle chambers to contract. When the action potential causes a single atrial contraction followed by a single ventricular contraction the heart is displaying a one-to-one atrial to ventricular response. In other words, for a given atrial contraction, the cardiac signal causing the atrial contraction subsequently causes a ventricle contraction. In this manner, there is a one-to-one atrial to ventricular response. Cardiac conditions also exist where the action potential moves in a retrograde direction, where the cardiac signal moves from the ventricular chamber up into the atrial chamber.

When a patient's heart rate increases to above 100 beats per minute, the patient is said to be experiencing a tachyarrhythmia. Many different types of tachyarrhythmias can exist. For example, a heart in a sinus tachycardia (heart rates between 100–180 beats per minute) exhibits a normal cardiac cycle, where action potential moves in the antegrade direction from the atrial chambers to the ventricular chambers to cause the contraction of the heart. The increased heart rate during the sinus tachycardia is a response to a stimulus, and not to a cause within the heart. For example, sinus tachycardia stimulus can include physiologic responses to maintain adequate cardiac output and tissue oxygenation during exercise. Unlike sinus tachycardia, a ventricular tachycardia (heart rates between 120–250) is caused by electrical disturbances within the heart, and not due to the physiological demands of the body. Ventricular tachycardias must be treated quickly in order to prevent the tachycardia from degrading into a life threatening ventricular fibrillation.

Distinguishing a ventricular tachycardia from a sinus tachycardia is important for diagnosing and properly treating the patient's cardiac condition. Misdiagnosis of a sinus tachycardia as a ventricular tachycardia can lead to inappropriate treatment. Difficulty in distinguishing among tachyarrhythmias increases when the heart is displaying a one-to-one atrial to ventricular rhythm. One reason for this difficulty is that the action potentials generated during the tachyarrhythmia can travel either in the antegrade direction, from the atria to the ventricles, or in a retrograde direction, from the ventricles into the atria. Tachyarrhythmias having action potentials conducted in an antegrade direction include sinus tachycardia and atrial tachycardia. Tachyarrhythmias having action potentials conducted in a retrograde direction include ventricular tachycardia with 1-to-1 retrograde conduction. Distinguishing the direction of the action potential (antegrade or retrograde) during a tachyarrhythmia is important in diagnosing and delivering the appropriate type of treatment to the patient.

For the reasons stated above, and for other reasons stated below which will become apparent to those skilled in the art upon reading and understanding the present specification, there is a need in the art for a reliable and convenient approach which can distinguish antegrade and retrograde action potentials during a tachyarrhythmia.

SUMMARY OF THE INVENTION

The present subject matter provides a system and a method for distinguishing antegrade from retrograde action potentials during a tachyarrhythmia episode. The classified action potentials are then used to classify the tachyarrhythmia episode as occurring in either a retrograde direction or an antegrade direction.

In one embodiment, both atrial and ventricular contractions are detected in sensed cardiac signals. The detected atrial and ventricular contractions are then used to determine atrial and ventricular cycle lengths. In one embodiment, an atrial cycle length is the time between successively sensed atrial contractions, and a ventricular cycle length is the time between successively sensed ventricular contractions. The ventricular contractions are further analyzed to determine the occurrence of a tachycardia episode.

When a tachycardia episode is detected, the sensed atrial and ventricular contractions are analyzed to determine if the contractions have a one-to-one association of atrial contractions to ventricular contractions. During a tachycardia episode having a one-to-one association of atrial contractions to ventricular contractions, the atrial cycle lengths are paired with the ventricular cycle lengths. In one embodiment, the atrial cycle lengths are paired with the ventricular cycle lengths in the antegrade direction. In pairing the cycle lengths in the antegrade direction, an atrial cycle length is paired with a ventricular cycle length that starts just after the start of the atrial cycle length. In pairing the cycle lengths in the retrograde direction, the atrial cycle length is paired with the ventricular cycle length that starts just before the start of the atrial cycle length.

In one embodiment, as the atrial and ventricular cycle lengths are paired in the antegrade and the retrograde directions the difference of the paired cycle lengths is calculated. The differences of the paired cycle lengths are then used to calculate correlation coefficients for both the cycle lengths paired in the antegrade direction and the retrograde direction. Based on the value of the correlation coefficients, the tachycardiac episode is then classified based on the values of the antegrade correlation coefficient and the retrograde correlation coefficient.

In one embodiment, the tachycardia episode is classified as occurring in a retrograde direction when the retrograde correlation coefficient is greater then the antegrade correlation coefficient. Alternatively, the tachycardia episode is classified as occurring in an antegrade direction when the antegrade correlation coefficient is greater then the retrograde correlation coefficient.

In addition to pairing atrial and ventricular cycle lengths in the antegrade and retrograde directions, the atrial and ventricular cycle lengths can also be paired in a super-antegrade and a super-retrograde direction. In one embodiment, atrial and ventricular cycle lengths are paired in the super-antegrade direction when an atrial cycle length is paired with a first ventricular cycle length started from an action potential causing the second atrial contraction of the atrial cycle length. The atrial and ventricular cycle lengths are paired in the super-retrograde direction when an atrial cycle length is paired with a second ventricular cycle length, the second ventricular cycle length having ended before the first atrial contraction of the atrial cycle length.

As the atrial and ventricular cycle lengths are paired in the super-antegrade and the super-retrograde directions the difference of the paired cycle lengths is calculated. The differences of the paired cycle lengths are then used to calculate correlation coefficients for both the cycle lengths paired in the super-antegrade direction and the super-retrograde direction. Based on the value of the correlation coefficients, the tachycardiac episode is then classified based on the values of the super-antegrade correlation coefficient and the super-retrograde correlation coefficient. Alternatively, the tachycardiac episode is then classified based on the values of the antegrade, super-antegrade, retrograde and super-retrograde correlation coefficients.

In one embodiment, the tachycardia episode is classified as occurring in a retrograde direction when the super-retrograde correlation coefficient is greater then the super-antegrade correlation coefficient. Alternatively, the tachycardia episode is classified as occurring in an antegrade direction when the super-antegrade correlation coefficient is greater then the super-retrograde correlation coefficient.

BRIEF DESCRIPTION OF THE DRAWINGS

FIG. 8 is a schematic illustrating one embodiment of a super-antegrade pairing of atrial and ventricular cycle lengths;

FIG. 9 is a schematic illustrating one embodiment of a super-retrograde pairing of atrial and ventricular cycle lengths;

DETAILED DESCRIPTION

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments illustrated herein are demonstrated in an implantable cardiac defibrillator (ICD), which may include numerous defibrillation, pacing, and pulse generating modes known in the art. However, these embodiments are illustrative of some of the applications of the present system, and are not intended in an exhaustive or exclusive sense. The concepts described herein can be used in a variety of applications which will be readily appreciated by those skilled in the art upon reading and understanding this description. For example, the present system is suitable for implementation in a variety of implantable and external medical devices.

As discussed above, discriminating one-to-one rhythms conducted in an antegrade direction (e.g., sinus tachycardia, atrial tachycardia) from one-to-one rhythms conducted in a retrograde direction (e.g., VT with one-to-one retrograde conduction) is important aspect of properly diagnosing a tachyarrhythmia episode. The present subject matter utilizes sensed cardiac complexes in determining, or distinguishing, the conduction direction of the cardiac signal. Cardiac complexes include the electrical excitatory impulses, or action potentials, that are sensed from the heart is it goes through the cardiac cycle.

The present subject matter uses the sensed cardiac complexes in a process called Cross Chamber Interval Correlation (CCIC). CCIC discriminates and classifies tachyarrhythmias displaying a one-to-one atrial to ventricular rhythm as either being conducted in an antegrade direction or in a retrograde direction. In one embodiment, atrial cycle lengths and ventricular cycle lengths are used in determining whether the tachyarrhythmia is being conducted in the antegrade or retrograde direction. An atrial cycle length is the time between successively sensed atrial contractions. In one embodiment, the sensed atrial contractions are the P-waves of a sensed electrocardiogram signal. A ventricular cycle length is the time between successively sensed ventricular contractions. In one embodiment, the sensed ventricular contractions are the R-waves of a sensed electrocardiogram signal.

Figure 1:
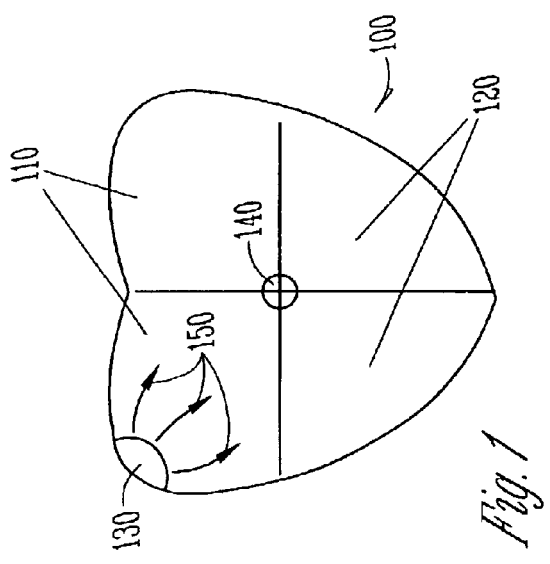
FIG. 1 is a schematic of a heart.

FIG. 1 shows a drawing of a human heart 100. The heart 100 is divided into atrial chambers 110 and ventricular chambers 120. When the heart 100 is in normal sinus rhythm or in sinus tachycardia the contractile wave (action potential) for the heart beat originates in the SA node 130, which is located in the atrial region of the heart 100. In this situation the atrial chambers 110 can be though of as originating the signals to start the contraction of the heart 100. The contractile wave moves from the SA node 130 across the atria and then to the AV node 140. Lines 150 show the direction of the contractile wave as it would move across the atrial chambers 110. The AV node consists of small specialized cells located on the right side of the atrial septum just under the endocardium. The lower portion of the AV node consists of parallel fibers that form the only "bridge" of contiguous cardiac cells crossing the cartilaginous structure that provides support for the cardiac valves and electrically separates atria from ventricles. Propagation of the impulse through this AV nodal region is typically very slow (approximately 0.05 m/s) and therefore a delay is imposed between excitation of the atria and the ventricles. The term AV delay is given to denote this delay. The action potential causing the contractile wave then moves through the AV node and down into the ventricle chambers 120. The contractile wave is distributed quickly and essentially evenly through out the ventricle chambers 120 which allows for near simultaneous contraction of ventricles of the heart 100.

When the contractile wave originates in the SA node and moves through the AV node into the ventricles, the contractile wave is said to be moving in an antegrade direction. Examples of when the contractile wave is moving in the antegrade direction include when the heart is in normal sinus rhythm or when the heart is in sinus tachycardia. There are also cardiac conditions in which the contractile wave, or action potential, can move in a retrograde direction. In this situation the cardiac signal moves from the ventricular chamber up into the atrial chamber. An example of a cardiac condition displaying a retrograde direction is ventricular tachycardia with 1-to-1 retrograde conduction.

When a tachyarrhythmia displaying a one-to-one atrial to ventricular cycle length is detected, sensed atrial cycle lengths are paired with and compared with sensed ventricular cycle lengths. One way of comparing paired atrial cycle lengths and ventricular cycle lengths is in an antegrade direction. Another way of comparing paired atrial cycle lengths and ventricular cycle lengths in is a retrograde direction.

Figure 2:
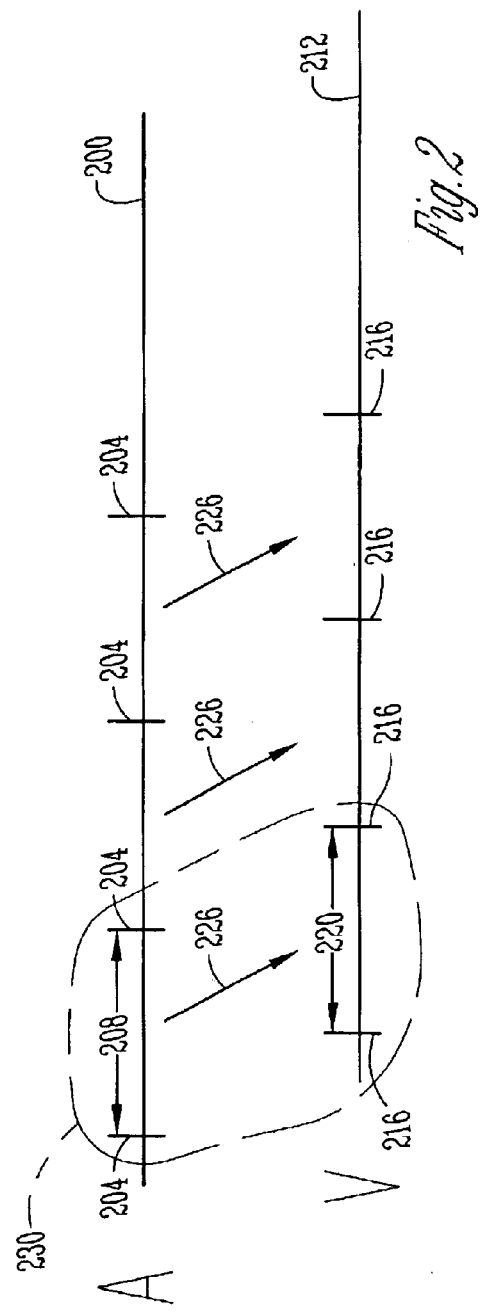
FIG. 2 is a schematic illustrating one embodiment of an antegrade pairing of atrial and ventricular cycle lengths.

In one embodiment, antegrade pairing and comparing is accomplished by pairing an atrial cycle length with at least one ventricular cycle length started after the start of the atrial cycle length being paired. FIG. 2 shows one embodiment of an antegrade pairing of atrial and ventricular cycle lengths. At 200 there is shown atrial cycle lengths, where 204 indicates the occurrence of atrial contraction. In one embodiment, the atrial contractions are indicated by the sensing of an electrocardiogram P-wave. An atrial cycle length (or P—P-wave interval) constitutes the time between successive atrial contractions as indicated by 208. At 212 there is shown ventricular cycle lengths, where 216 indicates the occurrence of ventricular contraction. In one embodiment, the ventricular contractions are indicated by the sensing of an electrocardiogram R-wave. An ventricular cycle length (or R—R wave interval) constitutes the time between successive ventricular contractions as indicated by 220.

When a tachyarrhythmia having a one-to-one atrial to ventricular cycle length is detected, atrial cycle lengths 208 are paired with and compared to ventricular cycle lengths 220 in the antegrade direction 226. When atrial cycle lengths 208 and ventricular cycle lengths 220 are paired in the antegrade direction, the atrial cycle length 208 is paired with a ventricular cycle length 220 started after the start of the atrial cycle length being paired. An example of a pairing is shown by the enclosed area 230.

Figure 3:
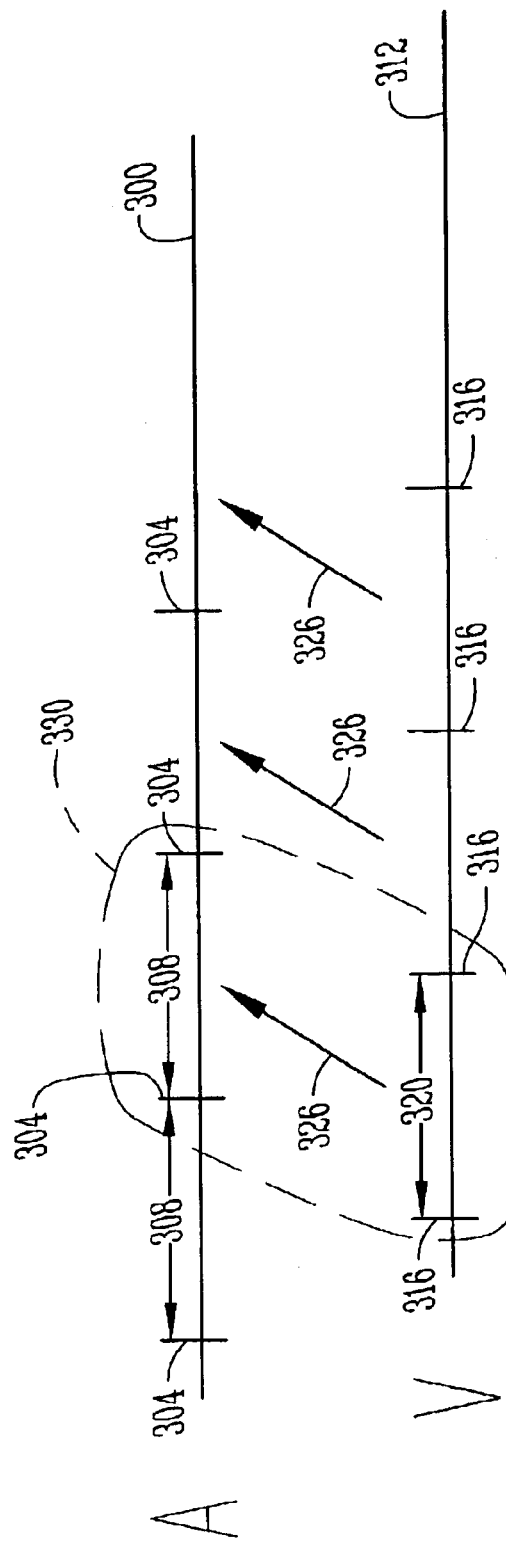
FIG. 3 is a schematic illustrating one embodiment of a retrograde pairing of atrial and ventricular cycle lengths.

In addition to pairing and comparing in the antegrade direction, the same atrial cycle lengths and ventricular cycle lengths can be paired and compared in a retrograde direction. For the retrograde direction, atrial cycle lengths are paired with ventricular cycle lengths started before each atrial cycle length being paired. FIG. 3 shows one embodiment of an retrograde pairing of atrial and ventricular cycle lengths. At 300 there is shown atrial cycle lengths, where 304 indicates the occurrence of atrial contraction. The atrial cycle length is indicated by 308. At 312 there are shown ventricular cycle lengths, where 316 indicates the occurrence of ventricular contraction. The ventricular cycle length is indicated by 320. During the tachyarrhythmia displaying a one-to-one atrial to ventricular cycle length, atrial cycle lengths 308 are paired with and compared to ventricular cycle lengths 320 in the retrograde direction 326. When atrial cycle lengths 308 and ventricular cycle lengths 320 are paired in the retrograde direction, the atrial cycle length 308 is paired with a ventricular cycle length 320 started before the start of the atrial cycle length being paired. An example of a pairing is shown by the enclosed area 330.

Correlation coefficients are then determined for the paired atrial cycle lengths and ventricular cycle lengths. A correlation coefficient describes the strength of an association between two variables. A high correlation coefficient implies a strong association so that the value of one variable can be used to predict, to some extent, the value of the other variable. In this invention the sequence of atrial cycle is one variable and the sequence of ventricular cycle lengths is the other variable. The correlation coefficient is computed using these sequences using both the antegrade pairing (as in FIG. 2) and the retrograde pairing (as in FIG. 3). Depending on the true direction of conduction, either the antegrade or retrograde pairing will have a higher correlation coefficient.

For example, a set of variable pairs, the correlation coefficient gives the strength of the association. For example, when the action potential is traveling in an antegrade direction during a one-to-one tachyarrhythmia, the atrial cycle lengths will more closely match the ventricular cycle lengths following the atrial cycle lengths, as the action potential initially causing atrial contraction is the action potential that subsequently causes the ventricular contraction. In this situation, the antegrade correlation coefficient will be larger than the retrograde correlation coefficient. On the other hand, when the action potential is traveling in the retrograde direction during a one-to-one tachyarrhythmia, the ventricular cycle lengths will more closely match the atrial cycle lengths following the ventricular cycle lengths, as the action potential initially causing the ventricular contraction is the action potential that subsequently causes the atrial contraction. In this situation, the retrograde correlation coefficient will be larger than the antegrade correlation coefficient.

Using the antegrade correlation coefficient and the retrograde correlation coefficient, the origin and conduction direction of a tachyarrhythmia can determined This information can then be used in making therapy determinations for the patient.

In one embodiment, cardiac complexes are sensed and analyzed using an ICD system. In one embodiment, the ICD system uses a dual chamber transvenous lead system to allow sensing of the cardiac action potentials in both the atrial chamber and the ventricular chamber. The transvenous lead system can include a ventricular lead and an atrial lead. In one embodiment, the ventricular lead has a rate-sensing (or near-field) electrode positioned at a distal end of the ventricular lead and at least one defibrillation electrode positioned along the surface of the lead. The atrial lead has a rate-sensing electrode positioned at a distal end of the atrial lead. In an additional embodiment, the atrial lead has at least two rate-sensing electrodes positioned along the peripheral surface of the atrial lead for rate-sensing. Other types of rate sensing electrodes are also considered appropriate to use with the present subject matter. Examples of other types of rate sensing electrodes include ring electrodes, both annular and semi-annular, as are known in the art. Rate sensing using the transvenous lead system can also be accomplished either through unipolar or bipolar sensing methods, as are known in the art.

In one embodiment, the ventricular lead system has a single defibrillation electrode. When a single defibrillation electrode is present, the ICD uses unipolar sensing and defibrillation, as is known in the art. In one embodiment, a ventricular lead is implanted within a heart, where the rate sensing electrode and the defibrillation electrode are positioned within the right ventricular chamber. In an alternative embodiment, the ventricular lead has at least two defibrillation electrodes. When two defibrillation electrodes are present, the ICD system can preform bipolar sensing far-field (or morphology) sensing the cardiac action potentials. In bipolar sensing, cardiac action potentials are sensed between the two defibrillation electrodes, and defibrillation electrical shocks are delivered between the two defibrillation electrodes. The ICD system of the present subject matter can also use endocardial and patch electrodes as are known in the art.

Figure 4:
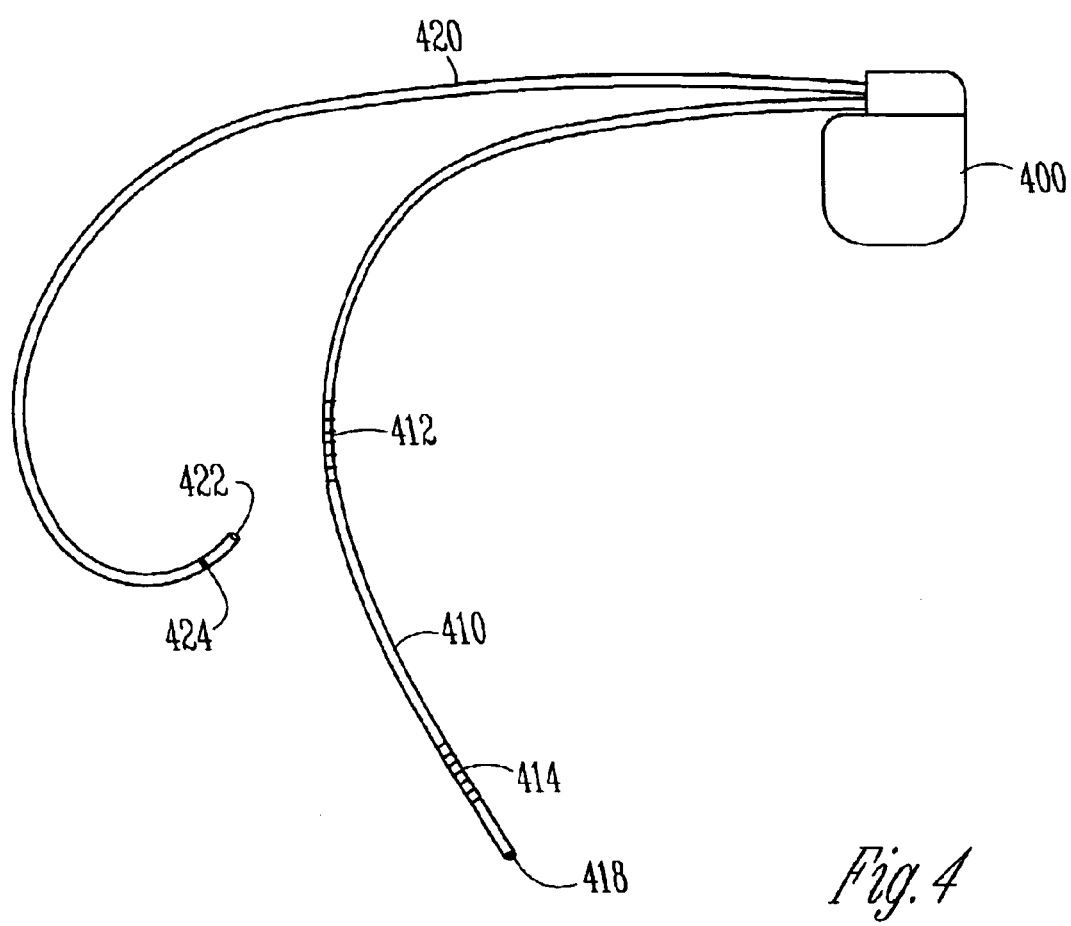
FIG. 4 is a schematic view of one embodiment of an implantable medical device according to one embodiment of the present subject matter.

One example of an appropriate system is shown in FIG. 4. ICD 400 is coupled to ventricular lead 410 and atrial lead 420. In one embodiment, the ventricular lead 410 includes a first defibrillation electrode 412, a second defibrillation electrode 414 and a ventricular pacing/sensing electrode 418. In an additional embodiment, the atrial lead 420 includes an first atrial pacing/sensing electrode 422 and a second atrial pacing/sensing electrode 424. Additionally, the housing of the ICD 400 is optionally used as an electrical pole for unipolar sensing and pulse delivery.

The ICD 400 senses cardiac signals, and when a tachyarrhythmic event is detected electronic circuitry within the ICD 400 analyze the sensed arrhythmic complexes (i.e., the cardiac signals) of the arrhythmic event. During the analysis, the ICD compares cycle lengths between contiguous pairs of cardiac events, or contractions, sensed from a first chamber of the heart (e.g. either the ventricular or the atrial chamber) to contiguous pairs of cardiac events, or contractions, sensed, or occurring, in the second chamber of the heart. Based on the comparison, the ICD 400 is able to distinguish the conduction as either being antegrade or retrograde, and depending upon the ICD's classification of the arrhythmic event.

Figure 5:
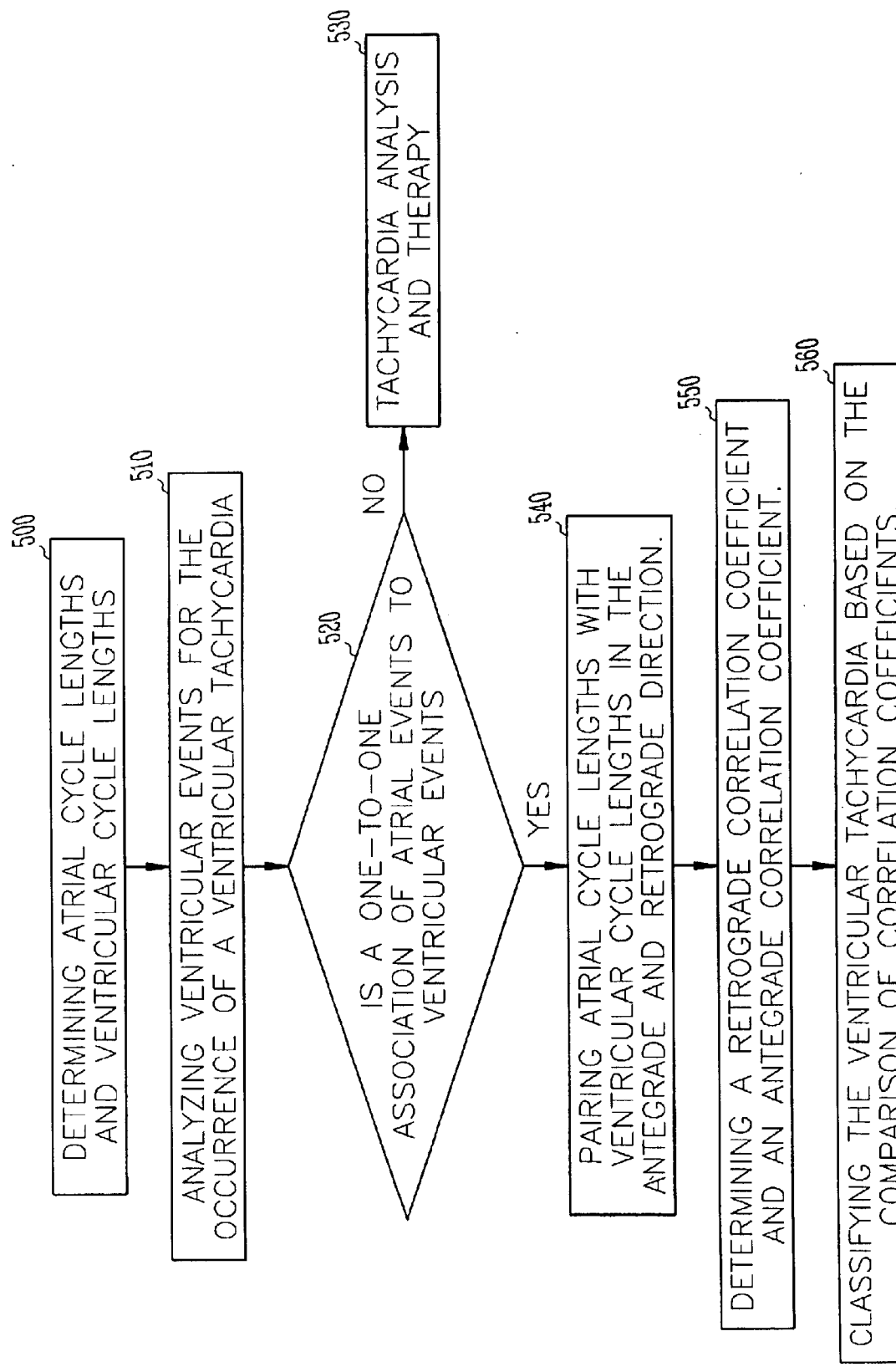
FIG. 5 is a flow chart illustrating one embodiment of the present subject matter.

Referring now to FIG. 5, there is shown one embodiment for discriminating physiologic 1:1 antegrade rhythms such as sinus tachycardia (ST) from pathologic 1:1 retrograde rhythms such as ventricular tachycardia (VT). One of the underlying concepts of the present subject matter is based on the observation that during cardiac rhythms characterized by 1:1 atrial-to-ventricular or ventricular-to-atrial association, the cycle length variations in the originating chamber are correlated to the cycle length variations in the responding chamber except for any accompanying delay in the conduction path. For example, delay in the conduction path may be due to the actions of the AV-node or other structures of the conduction path. The resulting observation is that the cycle length variations (R—R or A—A intervals) in the origination chamber are statistically correlated with the cycle length variations in the responding chamber.

At 500, atrial cycle lengths are determined from sensed atrial contractions, where an atrial cycle length is a time between a first atrial contraction and a second atrial contraction successively sensed. Also at 500, ventricular cycle lengths are determined from sensed ventricular contractions, where a ventricular cycle length is a time between a first ventricular contraction and a second ventricular contraction successively sensed. The sensed ventricular contractions are also analyzed for the occurrence of a tachycardia episode at 510.

When a tachycardia episode is encountered, the sensed cardiac complexes are analyzed at 520 to determine if there is a one-to-one association of atrial contractions to ventricular contractions. In one embodiment, to determine whether there is a one-to-one association of atrial contractions to ventricular, the system compares the sensed atrial and ventricular rates to determine if the rates are in a one-to-one association. In an additional embodiment, atrial and ventricular cycle length pairs are excluded if either differs from the previous cycle lengths by larger than a predetermined threshold value. In one embodiment, the predetermined threshold value is approximately 10% of mean cycle lengths. If the difference in cycle length values is larger than the predetermined threshold this is typically indicative of undersensing or oversensing by the system and the value is not considered in the one-to-one determination.

When there is not a one-to-one association, the tachycardia episode is analyzed and treated at 530 by other known protocols and methods. However, when a one-to-one association is detected, atrial cycle lengths are paired with the ventricular cycle lengths in the antegrade direction and in the retrograde direction at 540. As the atrial cycle lengths and the ventricular cycle lengths are paired, an antegrade correlation coefficient and a retrograde correlation coefficient are calculated at 550.

At 560, the tachycardia event is classified as occurring in either an antegrade direction or in a retrograde direction depending upon which correlation coefficient has the larger value. If the conduction is in the antegrade direction, then absolute value of the antegrade correlation coefficient will be greater than the absolute value of the retrograde correlation coefficient. Alternatively, the tachycardia event is classified as occurring in the retrograde direction when the absolute value of the retrograde correlation coefficient is greater then the absolute value of the antegrade correlation coefficient. In one embodiment, a test statistic is constructed and used to determine if the two correlation coefficients, draw from samples of sizes $n_1$ and $n_2$ respectively, differ significantly from each other. If the correlation coefficient in one direction is significantly larger than that in the other direction, the rhythm can be classified. In one embodiment, sample sizes, $n_1$ and $n_2$, are predetermined values in the range of 10 to 1000, where 10 is an appropriate sample size.

The correlation coefficients are then compared to determine if these two correlation coefficients are statistically different. In one embodiment, a Fisher Z transformation is used to determined if the correlation coefficients are statistically different. Based on the result of the statistical analysis, the one-to-one tachycardia episode is classified as either a sinus tachycardia or a ventricular tachycardia using the correlation coefficient that is closer to 1. Therefore, the CCIC can determine the origin and the conduction direction of the tachyarrhythmia using the antegrade correlation coefficient and the retrograde correlation coefficient. This information can then be used in making therapy determinations for the patient.

Figure 6:
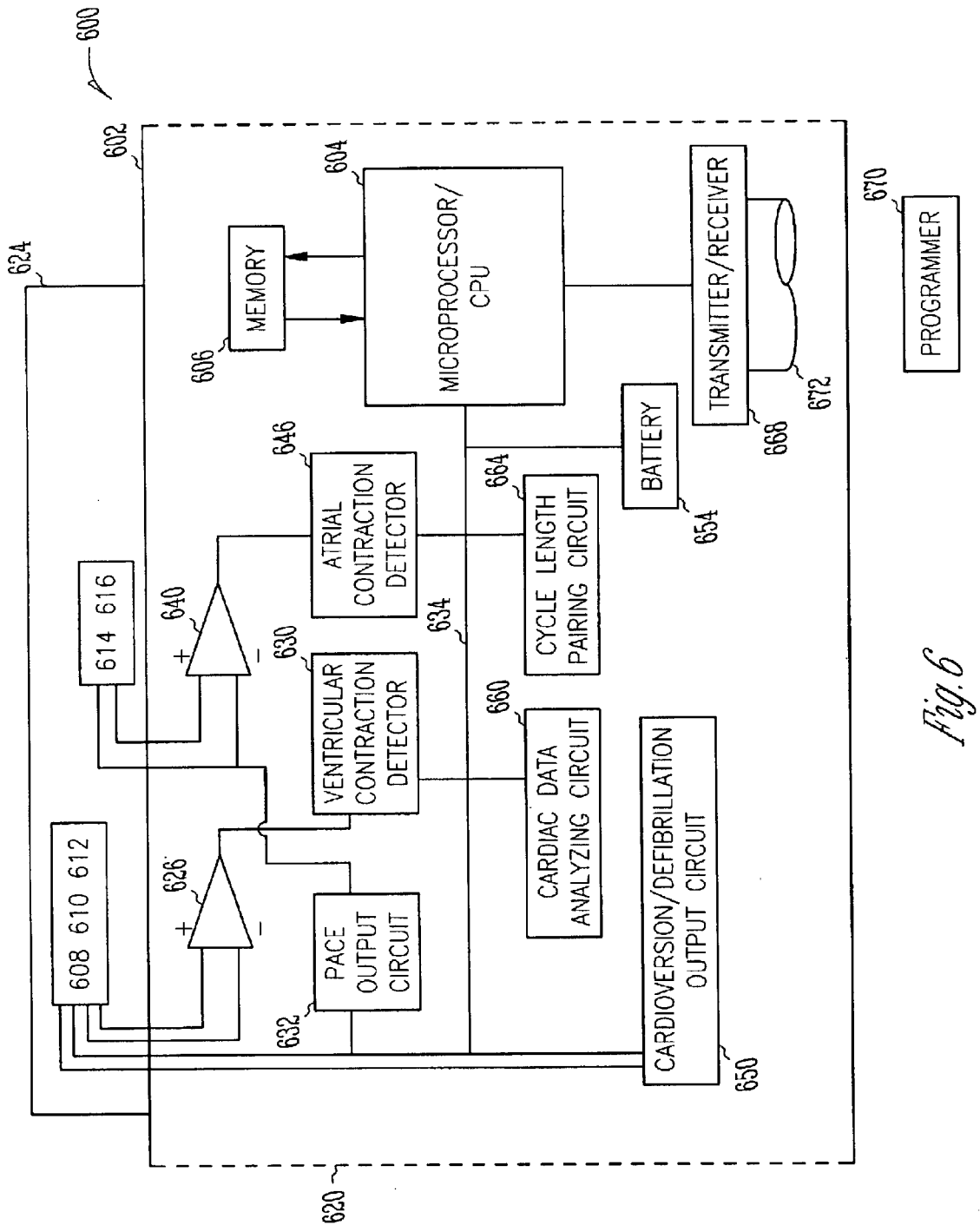
FIG. 6 is a block diagram of one embodiment of an implantable medical device according to the present subject matter.

Referring now to FIG. 6, there is shown an embodiment of a block diagram of an ICD 600 similar to ICD 400 shown in FIG. 4. The ICD 600 includes control circuitry 602 which receives one or more cardiac signals from the heart 430 (FIG. 4) and under predetermined conditions delivers electrical energy to the heart 430.

In one embodiment, the control circuitry 602 is a programmable microprocessor-based system, with a microprocessor 604 and a memory circuit 606, which contains parameters for various pacing and sensing modes and stores data indicative of cardiac signals received by the control circuitry 602. The control circuitry 602 includes terminals labeled with reference numbers 608, 610, 612, 614 and 616 for connection to the electrodes attached to the surface of the ventricular lead 410 and the atrial lead 420. In the present embodiment, the first defibrillation electrode 412 is coupled to terminal 608 through a first electrically insulated conductor provided within the ventricular lead 410. The second defibrillation electrode 414 is coupled to terminal 610 through a second electrically insulated conductor provided within the ventricular lead 410. The ventricular pacing/sensing electrode 418 on the ventricular lead 410 is coupled to terminal 612 through a third electrically insulated conductor provided within the ventricular lead 410. Finally, the first atrial pacing/sensing electrode 422 and the second atrial pacing/sensing electrode 424 are coupled to terminals 614 and 616, respectively, by electrically insulated conductors provided within the atrial lead 420.

The control circuitry 602 is encased and hermetically sealed in a housing 620 suitable for implanting in a human body. In one embodiment, the housing 620 is made of titanium, however, other biocompatible housing materials as are known in the art may be used. A connector block 624 is additionally attached to the housing 620 to allow for the physical and the electrical attachment of the ventricular lead 410, the atrial lead 420 and the electrodes to the ICD 600 and the encased control circuitry 602.

Sense amplifier 626 is coupled to the control circuitry 602, and is electrically coupled to terminal 608, 610 and 612 to allow for cardiac signals to be sensed between the ventricular pacing/sensing electrode 418 and second defibrillation electrode 414 or between the ventricular pacing/sensing electrode 418 and the housing 620 of the ICD 600. The output of the sense amplifier 626 is connected to a ventricular contraction detector 630. In one embodiment, these components serve to sense and amplify ventricular contractions, for example by sensing ventricular R-waves, and apply signals indicative thereof to microprocessor 604. Among other things, the microprocessor 604 responds to the ventricular contraction detector 630 by providing pacing signals to a pace output circuit 632 via bus 634, as needed according to the programmed pacing mode. In one embodiment, the pace output circuit 632 then provides output pacing signals to terminals 610 and 612.

Sense amplifier 640 is coupled to the control circuitry 602, and is electrically coupled to terminal 614 and 616 to sense cardiac signals between the first atrial pacing/sensing electrode 422 and the second atrial pacing/sensing electrode 424. The output of the sense amplifier 640 is connected to an atrial contraction detector 646. In one embodiment, these components serve to sense and amplify atrial contractions, for example by sensing atrial P-waves, and apply signals indicative thereof to microprocessor 604. Among other things, the microprocessor 604 can respond to the atrial contraction detector 646 by providing pacing signals to the pace output circuit 632 via bus 634, as needed according to the programmed pacing mode. Pace output circuit 632 provides output pacing signals to terminals 614 and 616.

The first defibrillation electrode 412, the second defibrillation electrode 414 and the housing 620 are coupled to a cardioversion/defibrillation output circuit 650 to provide pulses of either cardioversion or defibrillation electrical energy to the terminals 610 or 608 and the housing 620 under the control of the microprocessor 604. Power to the ICD 600 is supplied by an electrochemical battery 654 that is housed within the ICD 600.

The control circuitry 600 further includes a cardiac data analyzing circuit 660, which is coupled to the microprocessor 604 and the memory circuit 606 via bus 634. In one embodiment, the cardiac data analyzing circuit 660 determines, or calculates, atrial cycle lengths from the sensed atrial contractions. In addition to determining atrial cycle lengths, the cardiac data analyzing circuit 660 also determines ventricular cycle lengths from the sensed ventricular contractions. Finally, the cardiac data analyzing circuit 660 analyzes ventricular contractions for the occurrence of a tachycardia episode, where the circuit is able to detect tachycardia episodes that have a one-to-one association of atrial contractions to ventricular contractions.

When a tachycardia episode having a one-to-one association of atrial contractions to ventricular contractions is detected, the atrial cycle lengths and the ventricular cycle lengths are paired by a cycle length pairing circuit 664. The cycle length pairing circuit 664 is coupled to the control circuitry 602 via the bus 634. The cycle length pairing circuit 664 receives the atrial and ventricular cycle lengths from the cardiac data analyzing circuit 660 and pairs the atrial cycle lengths with the ventricular cycle lengths. In one embodiment, the cycle length pairing circuit 664 pairs the atrial and ventricular cycle lengths in both the antegrade and retrograde directions. Additionally, the cycle length pairing circuit 664 can also pair the atrial and ventricular cycle lengths in a super-antegrade and a super-retrograde direction as will be described in greater detail later.

From the paired atrial and ventricular cycle lengths, the cycle length pairing circuit 664 determines a retrograde correlation coefficient for the atrial cycle lengths paired with the ventricular cycle lengths paired in the retrograde direction, and an antegrade correlation coefficient for the atrial cycle lengths paired with the ventricular cycle lengths in the antegrade direction. Additionally, the cycle length pairing circuit 664 can determine a super-retrograde and super-antegrade correlation coefficient, as will be discussed in greater detail later. The microprocessor 604 then compares the values of the correlation coefficients (retrograde vs. antegrade and/or super-retrograde vs. super-antegrade) and classifies the tachycardia episode based on the values of the correlation coefficients. In one embodiment, the microprocessor classifies the tachycardia episode as occurring in the retrograde direction when the retrograde correlation coefficient is greater then the antegrade correlation coefficient. Alternatively, the microprocessor 604 classifies the tachycardia episode as occurring in the antegrade direction when the antegrade correlation coefficient is greater then the retrograde correlation coefficient.

In an additional embodiment, once a tachycardia episode having a one-to-one association of atrial contractions to ventricular contractions has been identified, the microprocessor controls the pacing output circuit 632 to deliver a series of pacing pulses at a predetermine timing to the terminal connectors 608 and 610. Alternatively, once a tachycardia episode having a one-to-one association of atrial contractions to ventricular contractions has been identified, the microprocessor controls the pacing output circuit 632 to deliver a series of pacing pulses at a predetermine timing to the terminal connectors 614 and 616.

Electronic communication circuitry 668 is additionally coupled to the control circuitry 602 to allow the ICD 600 to communicate with an external controller 670. In one embodiment, the electronic communication circuitry 668 includes a data receiver and a data transmitter to send and receive and transmit signals and cardiac data to and from an external programmer 670. In one embodiment, the data receiver and the data transmitter include a wire loop antenna 672 to establish a radio frequency telemetric link, as is known in the art, to receive and transmit signals and data to and from the programmer unit 670.

Figure 7:
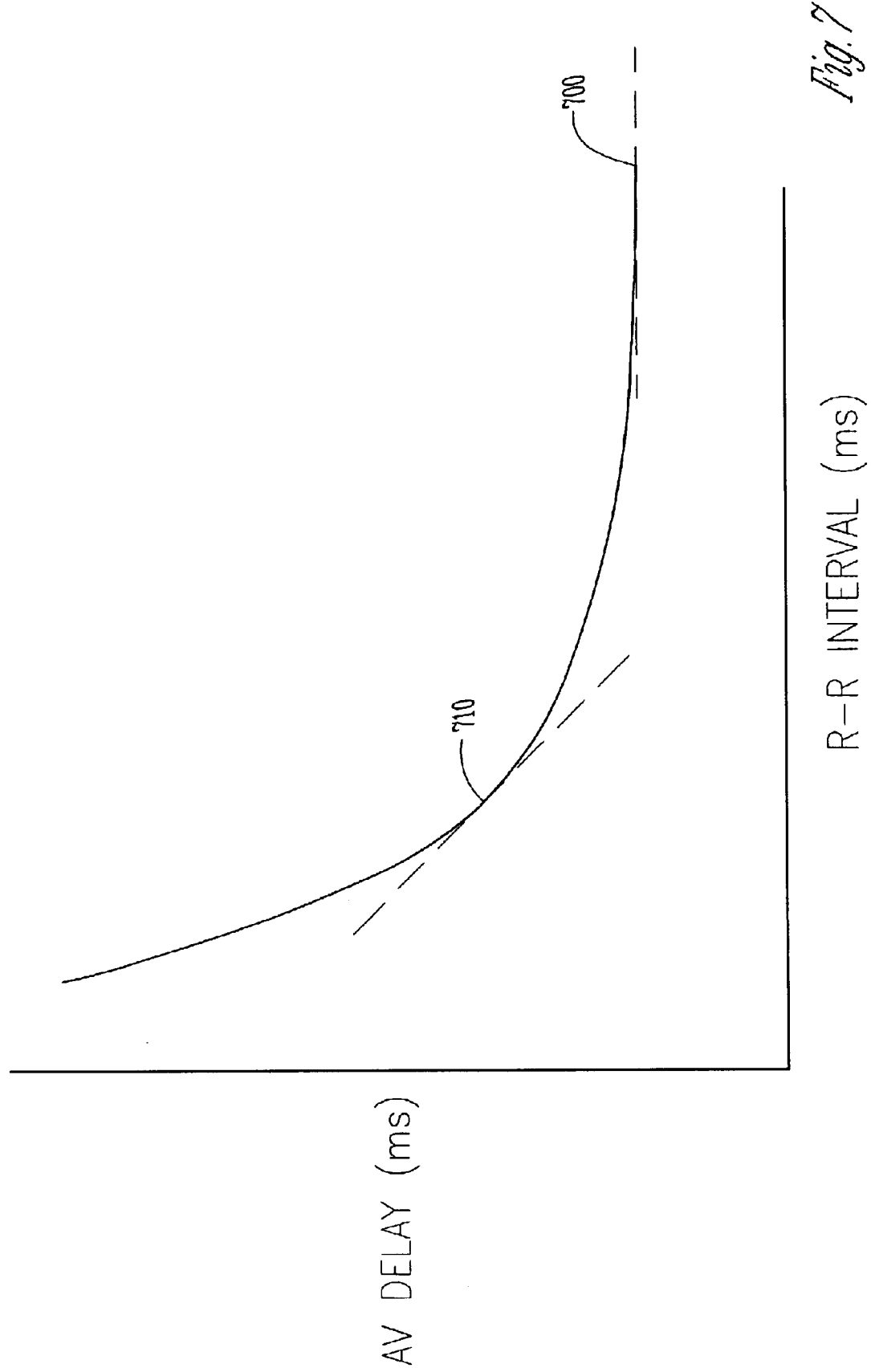
FIG. 7 is one embodiment of a curve showing the association of AV interval delay time to ventricular cycle length time.

The correlation between atrial and ventricular cycle lengths using antegrade and retrograde pairings is relatively easy to see when the delay across the AV node is constant or nearly constant. However, FIG. 7 shows a typical property of a human AV node. It plots the AV conduction time versus the R—R interval. When the R—R intervals are large (i.e., lower heart rates, approximately 60 to 100 beats/minute) the AV conduction curve has a slope that approaches zero. In FIG. 7, this area is shown at 700. On the other hand, when the R—R interval is decreased (i.e., at faster heart rates), the slope of the AV conduction curve becomes more negative. The section of the AV curves where the slope is approximately −1 is shown as area 710 in FIG. 7.

As the slope of the AV delay versus rate curve becomes negative, the delay required for an impulse to travel across the AV node gets longer and is more sensitive to the prematurity of the impulse. For example, at a R—R rate where the slope is −1, a contraction that occurs 10 msec prematurely (i.e., the R—R interval since the last contraction is 10 msec shorter than the average) will require an additional 10 msec to cross the AV node thus reaching the responding chamber at the same time it would have had the contraction occurred without prematurity.

Even if the conduction was truly in the antegrade direction, this slope in the AV conduction curve would reduce the antegrade correlation coefficient so that both the antegrade and retrograde correlation coefficients would be small. The present invention deals with this problem by using a super-antegrade and super-retrograde pairing for the computations as described below.

When the conduction through the AV node is constant (0 slope of AV conduction curve), any variation of cycle lengths in the atria are directly reflected by a similar (and correlated) cycle length variation in those same beats in the ventricles. However, when the AV conduction delay is inversely correlated cycle length (as when the AV conduction curve has a −1 slope), then the variations in the atria are no longer correlated with the variation of those same beats in the ventricles. That is why the correlation coefficient using the antegrade pairing is reduced.

However, while it is not obvious, under the conditions of a −1 slope in the AV curve, variations in the atria cycle length are correlated with the ventricular cycle length variation of the NEXT beat rather than the same beat. Thus, in addition to the antegrade and retrograde pairing of atrial and ventricular cycle lengths, the invention also uses super-antegrade and super-retrograde pairings as described below. If the conduction is truly antegrade and the slope of the AV curve is −1, then the correlation coefficient using the super-antegrade pairing is expected to be approximately 1 while the correlation coefficients using the super-retrograde, antegrade, and retrograde pairing are all expected to be close to zero.

FIG. 8 shows one embodiment of atrial cycle lengths and ventricular cycle lengths in the super-antegrade association. In one embodiment, the super-antegrade pairs consist of a comparison between a first atrial cycle length, as calculated from a first atrial contraction and a second atrial contraction immediately following the first atrial contraction, and a ventricular cycle length that is started from the action potential that caused the second atrial contraction of the first atrial cycle length. At 800 there is shown atrial cycle lengths, where 804 indicates the occurrence of atrial contraction. An atrial cycle length (or P—P-wave interval) constitutes the time between successive atrial contractions as indicated by 808. At 812 there are shown ventricular cycle lengths, where 816 indicates the occurrence of ventricular contraction. An ventricular cycle length (or R—R wave interval) constitutes the time between successive ventricular contractions as indicated by 820.

When a tachyarrhythmia having a one-to-one atrial to ventricular cycle length is detected, atrial cycle lengths 808 are paired with and compared to ventricular cycle lengths 820 in the super-antegrade direction 826. When atrial cycle lengths 808 and ventricular cycle lengths 820 are paired in the super-antegrade direction, the atrial cycle length 808 is paired with the first full ventricular cycle length 820 started after the end of the atrial cycle length 808 being paired. An example of a super-antegrade pairing is shown by the enclosed area 830.

In addition to pairing and comparing in the super-antegrade direction, the same atrial cycle lengths and ventricular cycle lengths can be paired and compared in the super-retrograde direction. For the super-retrograde pairs, a comparison is made between a first ventricular contraction and a second ventricular contraction, caused by a first R-wave event and a second R-wave event, respectively, and the time difference between a third R-wave event and a fourth R-wave event following the first and second R-wave events. For the super-retrograde direction, atrial cycle lengths are paired with ventricular cycle lengths that have ended before the start of the atrial cycle lengths they are being paired with. FIG. 9 shows one embodiment of a super-retrograde pairing of atrial and ventricular cycle lengths. At 900 there is shown atrial cycle lengths, where 904 indicates the occurrence of atrial contraction. The atrial cycle length is indicated by 908. At 912 there are shown ventricular cycle lengths, where 916 indicates the occurrence of ventricular contraction. The ventricular cycle length is indicated by 920. During the tachyarrhythmia displaying a one-to-one atrial to ventricular cycle length, atrial cycle lengths 908 can be paired with and compared to ventricular cycle lengths 920 in the super-retrograde direction 926. When atrial cycle lengths 908 and ventricular cycle lengths 920 are paired in the super-retrograde direction 926, the atrial cycle length 908 is paired with a ventricular cycle length 920 ending just prior to the start of the atrial cycle length being paired. An example of a pairing is shown by the enclosed area 930.

Correlation coefficients are then calculated for the super-antegrade and the super-retrograde pairings, and these values are used in conjunction with the correlation coefficients from the antegrade and retrograde pairings made for the same sensed atrial and ventricular cycle lengths. Using the correlation coefficients calculated from these four comparisons allows for an improved classification of the cardiac arrhythmia as being either in the antegrade or retrograde direction.

Figure 10:
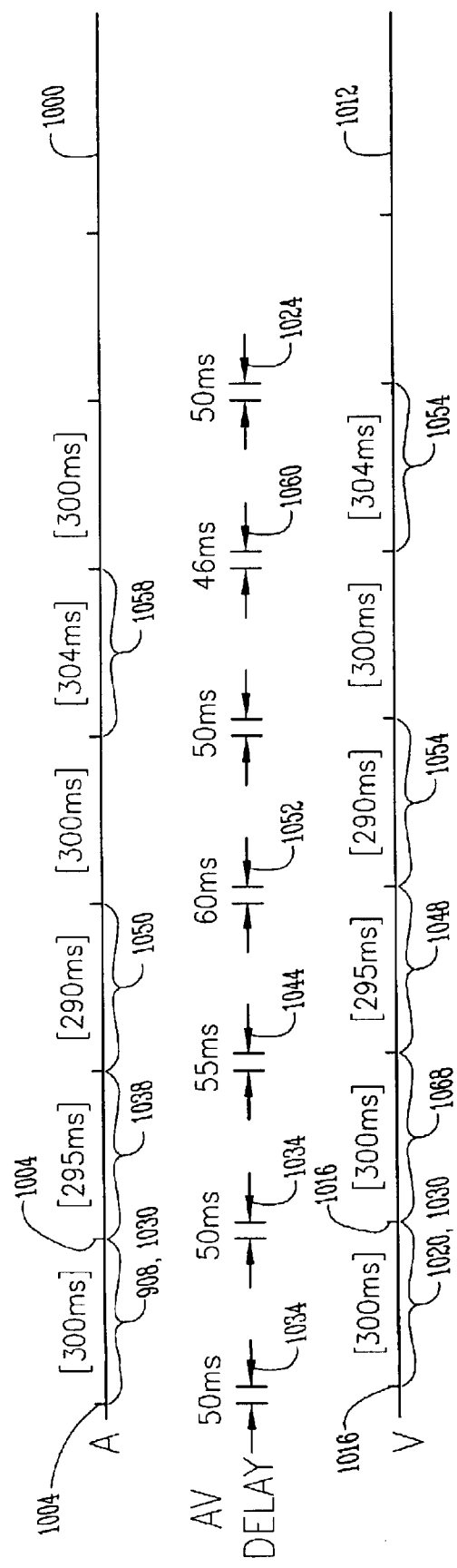
FIG. 10 is a schematic illustrating one embodiment of a super-antegrade pairing of atrial and ventricular cycle lengths.

FIG. 10 shows one embodiment of a super-antegrade comparison. At 1000 there is shown atrial cycle lengths, where 1004 indicates the occurrence of atrial contraction. An atrial cycle length (or P—P-wave interval) constitutes the time between successive atrial contractions as indicated by 1008. At 1012 there are shown ventricular cycle lengths, where 1016 indicates the occurrence of ventricular contraction. An ventricular cycle length (or R—R wave interval) constitutes the time between successive ventricular contractions as indicated by 1020. In the present embodiment, the atrial chamber is the originating chamber.

AV delay intervals are also shown in FIG. 10 at 1024. As previously discussed the AV delay interval is the time the contractile wave takes to move through the AV node after being received from the originating chamber. By way of example only, and not in any limiting way, in FIG. 10 it is assumed that the heart is initially in a steady state with an atrial and ventricular rate of approximately 300 milliseconds. 1030 shows an atrial cycle length 1008 and a ventricular cycle length 1020 where the atrial cycle length and the responding ventricular cycle length is approximately 300 milliseconds. Also by way of example only, and not in any limiting way, during the steady state condition, the AV delay interval is also at a steady state condition. In the present embodiment, the AV delay interval is 50 milliseconds for atrial cycle lengths of approximately 300 milliseconds. 1034 show an AV delay interval of 50 milliseconds for atrial cycle lengths of approximately 300 milliseconds.

As previously discussed, when the R—R-wave interval decreases (the heart rate increasing) the slope of the AV conduction curve may become more negative. As the slope becomes negative, the delay required for an impulse to travel across the AV node depends on the rate at which the node is being activated. When there is a premature contraction from the originating chamber, the resulting AV delay value is increased by a value that corresponds to the prematurity of the originating chamber. Likewise, when the contraction in the originating chamber causes the contraction cycle length to be longer than previously experienced, the AV delay value is decreased by approximately the same amount of time that the signal was early. As the slope of the AV conduction curve changes the values of the antegrade and retrograde correlation coefficients become less distinctive. The correlation coefficients from the super-antegrade and super-retrograde comparisons can then aid in making the determination between antegrade conduction and retrograde conduction.

By way of example only and not by way of limitation, in FIG. 10 it is assumed that the slope of the AV conduction curve is approximately −1. Therefore, changes in the originating chamber will be reflected inversely in the AV node delay. At 1038, there is a change in the atrial cycle length time from 300 milliseconds to 295 milliseconds. As this is a decrease in the atrial cycle length time, the contractile wave (or action potential) from the atrial chamber arrives at the AV node 5 milliseconds earlier than the steady state time. As the signal has arrived 5 milliseconds too early, there is a delay in the AV node of 5 milliseconds. So the total time for the contractile wave to move through the AV node is now 55 milliseconds as shown at 1044. The result is that the next subsequent ventricular cycle length is faster by 5 milliseconds. This faster ventricular cycle length is shown at 1048.

If the subsequent atrial cycle length is again faster than steady state (e.g., 290 milliseconds at 1050) there will be a inversely proportional delay through the AV node. So, for an atrial cycle length of 290 milliseconds at 1050 the delay through the AV node will be an additional 10 milliseconds bringing the total delay to 60 milliseconds as shown at 1052 (50 millisecond of the steady state delay plus the 10 millisecond additional delay). The result is that the next subsequent ventricular cycle length is faster by 10 milliseconds. This faster ventricular cycle length is shown at 1054.

Alternatively, at 1058 there is a change in the atrial cycle length time from 300 milliseconds to 304 milliseconds. As this is an increase in the atrial cycle length time, the contractile wave (or action potential) from the atrial chamber arrives at the AV node 4 milliseconds later than the steady state time. As the signal has arrived 4 milliseconds later, there is a increase in the AV node delay of 4 milliseconds. So the total time for the contractile wave to move through the AV node is now 46 milliseconds as shown at 1060. The result is that the next subsequent ventricular cycle length is slower by 4 milliseconds. This slower ventricular cycle length is shown at 1064.

Looking at the antegrade and retrograde pairings for the atrial and ventricular cycle lengths in FIG. 10, it is evident that the correlation for these pairings begins to decrease. For example, the antegrade pairing of the atrial cycle length and ventricular cycle length for 1030 will still be well correlated. However, the atrial cycle length at 1038 and its antegrade pair at 1068 are no longer as well correlated as before (e.g., atrial cycle length of 295 ms and ventricular cycle length of 300 ms). The same goes for the remainder of the atrial cycle lengths and ventricular cycle lengths paired in the antegrade direction pairs. However, as the antegrade correlation values being to decrease, the super-antegrade correlation values will remain approximately the same. For example, in the super-antegrade direction the atrial cycle length 1030 and the ventricular cycle length at 1068 are well correlated. Similarly, the atrial cycle length at 1038 and the ventricular cycle length at 1048 are well correlated. This trend continues for the remainder of the atrial and ventricular cycle lengths paired in the super-antegrade direction. Thus, correlation coefficients for the super-antegrade and the super-retrograde pairings can be useful to further augment the antegrade and retrograde correlation coefficients.

Figure 11:
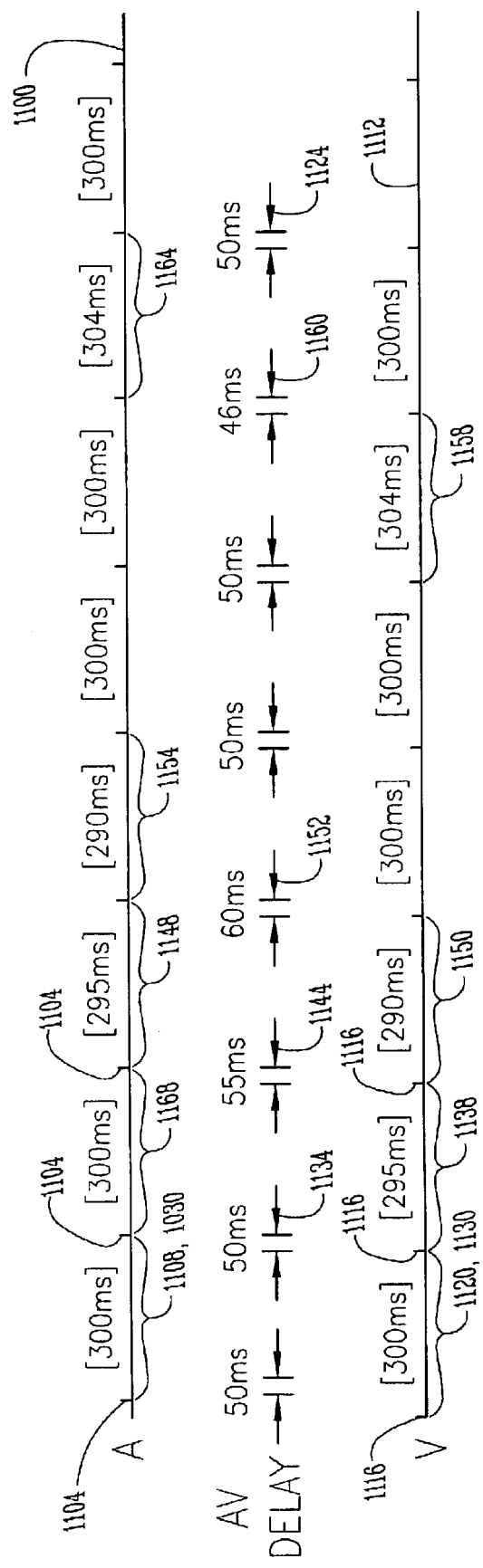
FIG. 11 is a schematic illustrating one embodiment of a super-retrograde pairing of atrial and ventricular cycle lengths.

FIG. 11 shows one embodiment of a super-retrograde comparison. At 1100 there is shown atrial cycle lengths, where 1104 indicates the occurrence of atrial contraction. 1108 shows an example of an atrial cycle length. At 1112 there are shown ventricular cycle lengths, where 1116 indicates the occurrence of ventricular contraction. 1120 shows an example of a ventricular cycle length. In the present embodiment, the ventricular chamber is the originating chamber.

AV delay intervals are also shown in FIG. 11 at 1124. By way of example only, and not in any limiting way, in FIG. 11 it is assumed that the heart is initially in a steady state with an atrial and ventricular rate of approximately 300 milliseconds. 1130 shows an atrial cycle length 1108 and a ventricular cycle length 1120 where the ventricular cycle length and the responding atrial cycle length is approximately 300 milliseconds. Also by way of example only, and not in any limiting way, during the steady state condition, the AV delay interval is also at a steady state condition. In the present embodiment, the AV delay interval is 50 milliseconds for ventricular cycle lengths of approximately 300 milliseconds. 1134 show an AV delay interval of 50 milliseconds for ventricular cycle lengths of approximately 300 milliseconds.

By way of example only and not by way of limitation, in FIG. 11 it is assumed that the slope of the AV conduction curve is approximately −1. Therefore, changes in the originating chamber will be reflected inversely in the AV node delay. At 1138, there is a change in the ventricular cycle length time from 300 milliseconds to 295 milliseconds. As this is a decrease in the ventricular cycle length time, the contractile wave (or action potential) from the ventricular chamber arrives at the AV node 5 milliseconds earlier than the steady state time. As the signal has arrived 5 milliseconds too early, there is a delay in the AV node of 5 milliseconds. So the total time for the contractile wave to move through the AV node is now 55 milliseconds as shown at 1144. The result is that the next subsequent atrial cycle length is faster by 5 milliseconds. This faster atrial cycle length is shown at 1148.

If the subsequent ventricular cycle length is again faster than steady state (e.g., 290 milliseconds at 1150) there will be an inversely proportional delay through the AV node. So, for a ventricular cycle length of 290 milliseconds at 1150 the delay through the AC node will be an additional 10 milliseconds bringing the total delay to 60 milliseconds as shown at 1152 (50 millisecond of the steady state delay plus the 10 millisecond additional delay). The result is that the next subsequent atrial cycle length is faster by 10 milliseconds. This faster atrial cycle length is shown at 1154.

Alternatively, at 1158 there is a change in the ventricular cycle length time from 300 milliseconds to 304 milliseconds. As this is an increase in the ventricular cycle length time, the contractile wave (or action potential) from the ventricular chamber arrives at the AV node 4 milliseconds later than the steady state time. As the signal has arrived 4 milliseconds later, there is an increase in the AV node delay of 4 milliseconds. So the total time for the contractile wave to move through the AV node is now 46 milliseconds as shown at 1160. The result is that the next subsequent atrial cycle length is slower by 4 milliseconds. This slower atrial cycle length is shown at 1164.

Looking at the antegrade and retrograde parings for the atrial and ventricular cycle lengths in FIG. 11, it is evident that the correlation for these pairings begins to decrease. For example, the retrograde paring of the ventricular cycle lengths and atrial cycle lengths for 1130 will still be well correlated. However, the ventricular cycle length at 1138 and its antegrade pair at 1168 are no longer as well correlated as before (e.g., ventricular cycle length of 295 ms and atrial cycle length of 300 ms). The same goes for the remainder of the atrial cycle lengths and ventricular cycle lengths paired in the antegrade direction. However, as the retrograde correlation values begin to decrease, the super-retrograde correlation values will remain approximately the same. For example, in the super-retrograde direction, the ventricular cycle length 1130 and the atrial cycle length at 1148 are well correlated. This trend continues for the remainder of the atrial and ventricular cycle lengths paired in the super-retrograde direction. Thus, correlation coefficients for the super-antegrade and the super-retrograde pairings can be useful to further augment the antegrade and retrograde correlation coefficients.

As described thus far, the present subject matter can use intrinsic variations in the originating and responding chambers. In one embodiment, a series of pacing pulses are delivered to the atrial chamber of the heart, where each pacing pulse of the series of pacing pulses is delivered at a predetermined frequency. In one embodiment, the predetermined frequency is variable, so that variability in the cycle lengths is introduced. As the pacing pulses are delivered with the predetermined frequency into the atrial chamber, cardiac signals, including cardiac complexes, from the ventricular chamber are sensed and analyzed to determine whether the variability is detected in the ventricular chambers. In one embodiment, the CCIC coefficient, as previously described, is used to determine whether the variability is detected in the responding chamber. In an alternative embodiment, the predetermined frequency is constant, so that essentially no variability in the cycle lengths is introduced. The CCIC coefficient is then used to determine what type of response is detected in the ventricular chamber.

In an alternative embodiment, a series of pacing pulses are delivered to the ventricular chamber, where each pacing pulse of the series of pacing pulses is delivered at a predetermined frequency. In one embodiment, the predetermined frequency is variable, so that variability in the cycle lengths is introduced. As the pacing pulses are delivered with the predetermined frequency into the ventricular chamber, cardiac signals, including cardiac complexes, from the atrial chamber are sensed and analyzed to determine whether the variability is detected in the atrial chambers. In one embodiment, the CCIC coefficient, as previously described, is used to determine whether the variability is detected in the responding chamber.

In an alternative embodiment, the predetermined frequency is constant, so that essentially no variability in the cycle lengths is introduced. The CCIC coefficient is then used to determine what type of response is detected in the atrial chamber.

Figure 12:
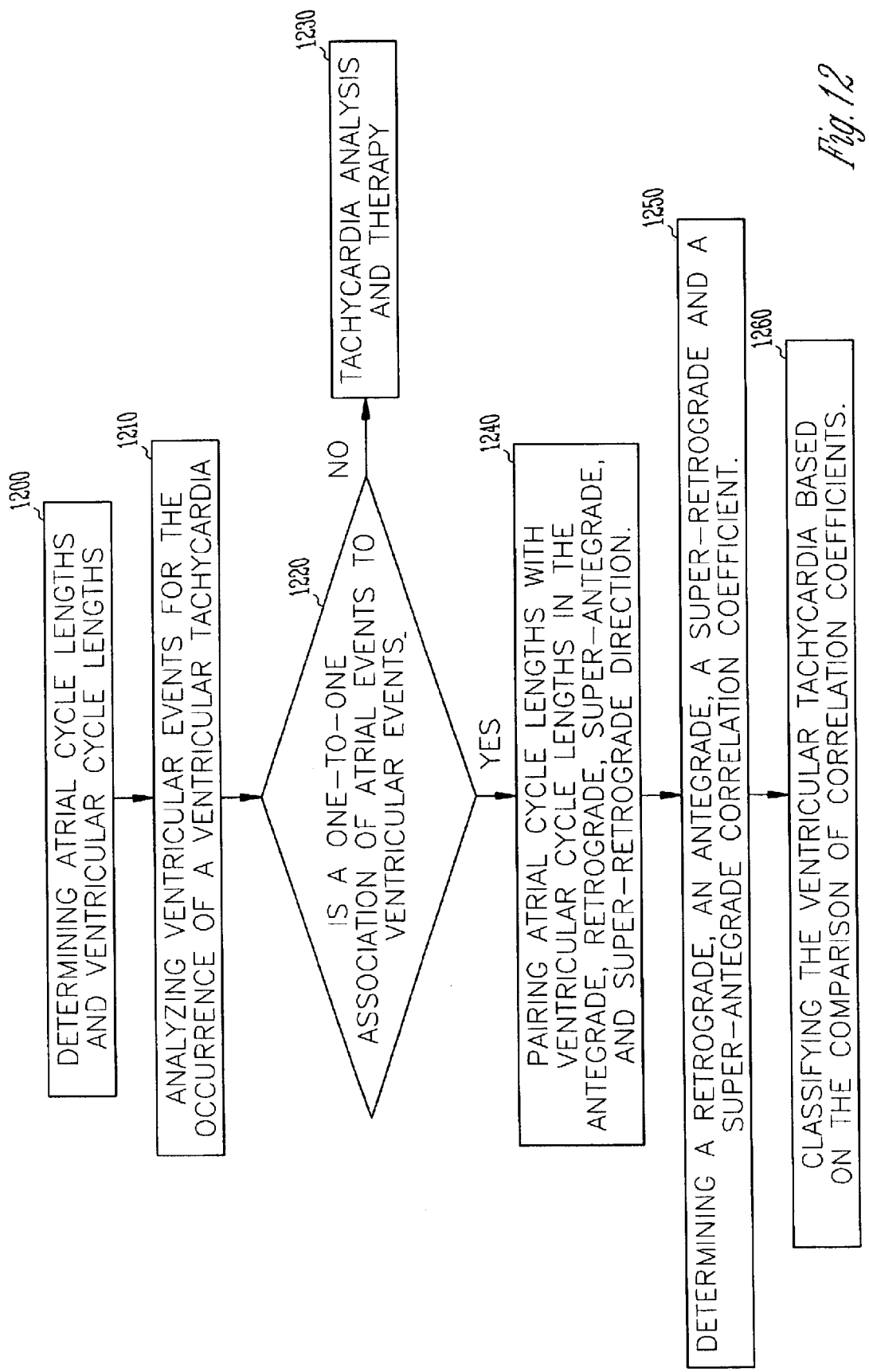
FIG. 12 is a flow chart illustrating one embodiment of the present subject matter.

Referring now to FIG. 12, there is shown an additional embodiment for discriminating physiologic 1:1 antegrade rhythms such as sinus tachycardia (ST) from pathologic 1:1 retrograde rhythms such as ventricular tachycardia (VT). At 1200, atrial cycle lengths and ventricular cycle lengths are determined as previously discussed. The sensed ventricular contractions are analyzed for the occurrence of a tachycardia episode at 1210. When a tachycardia episode is encountered, the sensed cardiac complexes are analyzed at 1220 to determine if there is a one-to-one association of atrial contractions to ventricular contractions. In an additional embodiment, besides determining that there is a one-to-one rhythm occurring, the stability of the AV interval is also tested to determine whether it is below a threshold (AV associated). In one embodiment, when the AV intervals are found to be stable (i.e., constant), the rhythm is more likely an associated rhythm.

In an additional embodiment, the atrial and ventricular cycle length pairs are checked by determining if they are within a predetermined error range. In one embodiment, the predetermined error range is approximately 10–50%, where 20% is an acceptable value. In an additional embodiment, atrial and ventricular cycle length pairs are excluded if either differs from the previous cycle lengths by larger than a predetermined threshold value. In one embodiment, the predetermined threshold value is in the range of approximately 5–20% where 10% is an acceptable value.

When there is not a one-to-one association, the tachycardia episode is analyzed and treated at 1230 by other known protocols and methods. However, when a one-to-one association is detected, atrial cycle lengths are paired with the ventricular cycle lengths in the antegrade direction, the retrograde direction, the super-antegrade direction and the super-retrograde direction at 1240. As the atrial cycle lengths and the ventricular cycle lengths are paired, the antegrade correlation coefficient, the retrograde correlation coefficient, the super-antegrade correlation coefficient and the Super-retrograde correlation coefficient are calculated at 1250.

At 1260, the tachycardia event is classified as occurring in either an antegrade direction or in a retrograde direction depending upon which correlation coefficient has the larger value as previously discussed. If a determination as to the direction cannot be made from the antegrade and retrograde correlation coefficients, the super-antegrade and super-retrograde correlation coefficients can be used in conjunction with the antegrade and retrograde correlation coefficients to make the determination. In one embodiment, when the correlation coefficients are not statistically different, then the super-antegrade and super-retrograde correlation coefficients are used to classify the direction of the tachycardia event.

Figure 13:
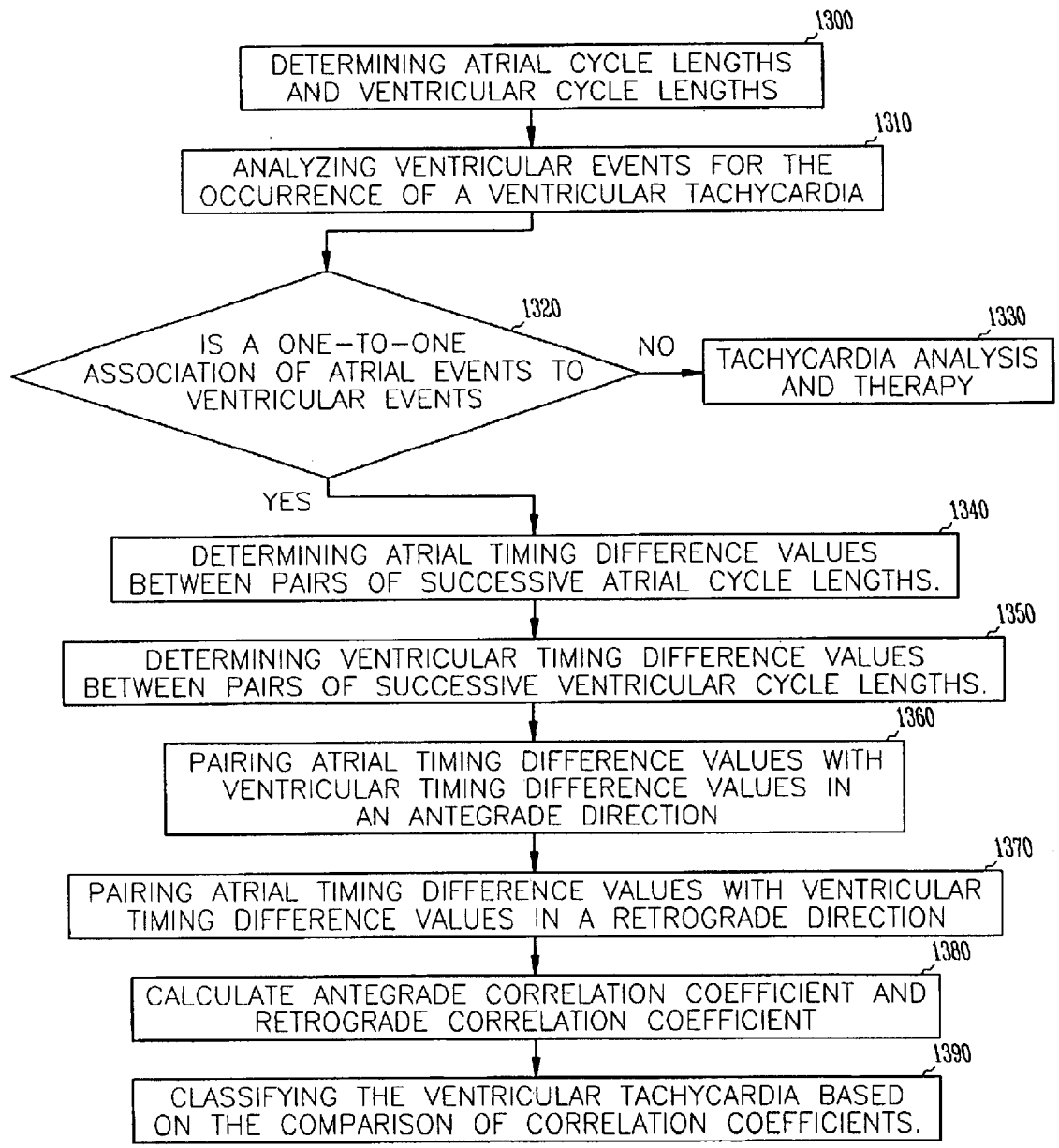
FIG. 13 is a flow chart illustrating one embodiment of the present subject matter.

Referring now to FIG. 13, there is shown an additional embodiment for discriminating physiologic 1:1 antegrade rhythms such as sinus tachycardia (ST) from pathologic 1:1 retrograde rhythms such as ventricular tachycardia (VT). At 1300, atrial cycle lengths and ventricular cycle lengths are determined as previously discussed. The sensed ventricular contractions are analyzed for the occurrence of a tachycardia episode at 1310. When a tachycardia episode is encountered, the sensed cardiac complexes are analyzed at 1320 to determine if there is a one-to-one association of atrial contractions to ventricular contractions.

When there is not a one-to-one association, the tachycardia episode is analyzed and treated at 1330 by other known protocols and methods. However, when a one-to-one association is detected, atrial timing difference values between pairs of successive atrial cycle lengths are determined at 1340. In one embodiment, atrial timing difference values are calculated by taking the atrial interval value of a second atrial interval and subtracting the atrial interval value of a first atrial interval, where the second atrial interval immediately follows the first atrial interval.

Figure 14:
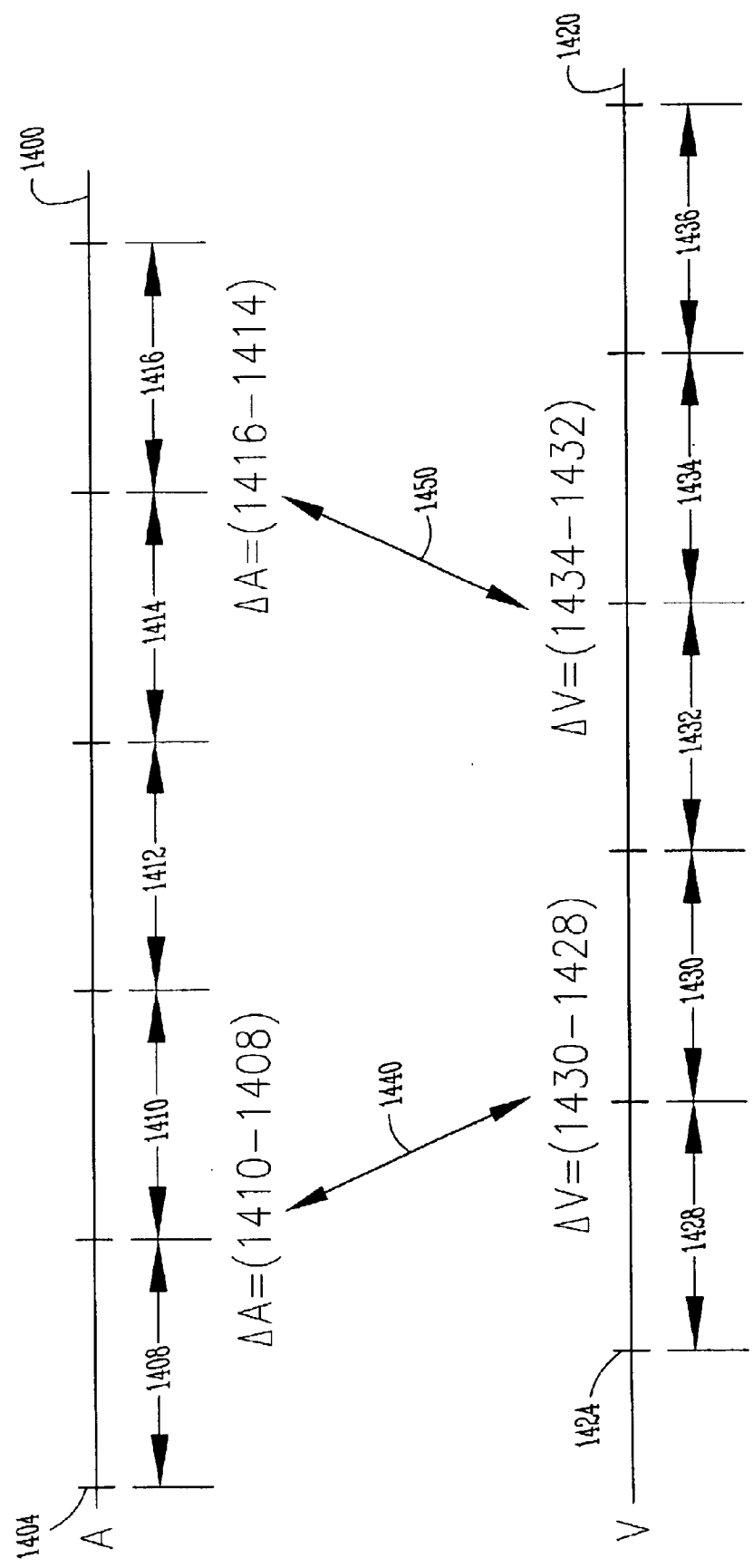
FIG. 14 is a schematic illustrating one embodiment of pairing of atrial and ventricular cycle lengths.

FIG. 14 shows one embodiment of determining atrial timing difference values. At 1400, there is shown atrial cycle lengths, where 1404 indicates the occurrence of atrial contractions and the atrial cycle lengths are shown at 1408, 1410, 1412, 1414 and 1416. In one embodiment, atrial timing difference values are calculated by taking the difference between atrial cycle length 1410 and atrial cycle length 1408, the difference between atrial cycle length 1412 and atrial cycle length 1410, atrial cycle length 1414 and atrial cycle length 1412, and atrial cycle length 1416 and atrial cycle length 1414.

In addition to determining atrial timing difference values, ventricular timing difference values are determined between pairs of successive ventricular cycle lengths. In one embodiment, ventricular timing difference values are calculated by taking the ventricular interval value of a second ventricular interval and subtracting the ventricular interval value of a first ventricular interval, where the second ventricular interval immediately follows the first ventricular interval.

FIG. 14 shows one embodiment of determining ventricular timing difference values. At 1420, there is shown ventricular cycle lengths, where 1424 indicates the occurrence of ventricular contractions and the ventricular cycle lengths are shown at 1428, 1430, 1432, 1434 and 1436. In one embodiment, ventricular timing difference values are calculated by taking the difference between ventricular cycle length 1430 and ventricular cycle length 1428, the difference between ventricular cycle length 1432 and ventricular cycle length 1430, ventricular cycle length 1434 and ventricular cycle length 1432, and ventricular cycle length 1436 and ventricular cycle length 1434.

Referring again to FIG. 13, the atrial timing difference values are then paired with the ventricular timing difference values in an antegrade direction at 1360. In one embodiment, atrial timing difference values paired with the ventricular timing difference values in an antegrade direction are shown at 1440 in FIG. 14. Atrial timing difference values are also paired with the ventricular timing difference values in a retrograde direction at 1370. In one embodiment, atrial timing difference values paired with the ventricular timing difference values in a retrograde direction are shown at 1450 in FIG. 14.

As the atrial timing difference values are paired with the ventricular timing difference values, the antegrade correlation coefficient and the retrograde correlation coefficient are calculated at 1380. At 1390, the tachycardia event is classified as occurring in either an antegrade direction or in a retrograde direction depending upon which correlation coefficient has the larger value as previously discussed. In an additional embodiment, if a determination as to the direction cannot be made from the antegrade and retrograde correlation coefficients, super-antegrade and super-retrograde correlation coefficients are determined and used in conjunction with the antegrade and retrograde correlation coefficients to make the determination. In one embodiment, when the correlation coefficients are not statistically different, then the super-antegrade and super-retrograde correlation coefficients are used to classify the direction of the tachycardia event.

In an additional embodiment, it is possible that some of the sensed cardiac signals display large differences in consecutive cycle lengths due to premature ventricular contractions or over/undersensing by the system. To prevent a few cardiac cycle lengths from dominating the correlation coefficient calculations, cycle lengths (or cycle length differences) are processed using a predetermined function to yield an integer value that represents the cycle length difference. In one embodiment, processing the cycle length differences includes assigning integer values to cycle length and/or cycle length differences having magnitudes that fall into predetermined ranges. In one embodiment, the cardiac data analyzing circuit is adapted to preform the predetermined function described herein.

In one embodiment, each of the atrial timing difference values are assigned an atrial integer value as a function of the magnitude of each of the atrial timing difference value. Additionally, each of the ventricular timing difference values is assigned a ventricular integer value as a function of the magnitude of each of the ventricular timing difference values. In one embodiment, when the magnitude of the ventricular timing difference value and/or the magnitude of the atrial timing difference value is approximately zero, the difference is represented by a zero (0). Additionally, when the magnitude of the ventricular timing difference value and/or the magnitude of the atrial timing difference value exceeds a first predetermined threshold, the difference is represented by a +1 or a −1, where a +1 represents a positive values of the difference between the intervals and a −1 represents a negative value of the difference between the intervals. In an additional embodiment, when the magnitude of the timing difference value and/or the magnitude of the atrial timing difference value exceeds a second predetermined threshold, the difference is represented by a +2 or a −2, where a +2 represents a positive values of the difference between the intervals and a −2 represents a negative value of the difference between the intervals. In one embodiment, the first predetermined threshold is a programmable value in the range of approximately 2 to 10 ms, where 2 ms is an acceptable value. In an additional embodiment, the second predetermined threshold is a programmable value larger than approximately 10 ms.

Figure 15:
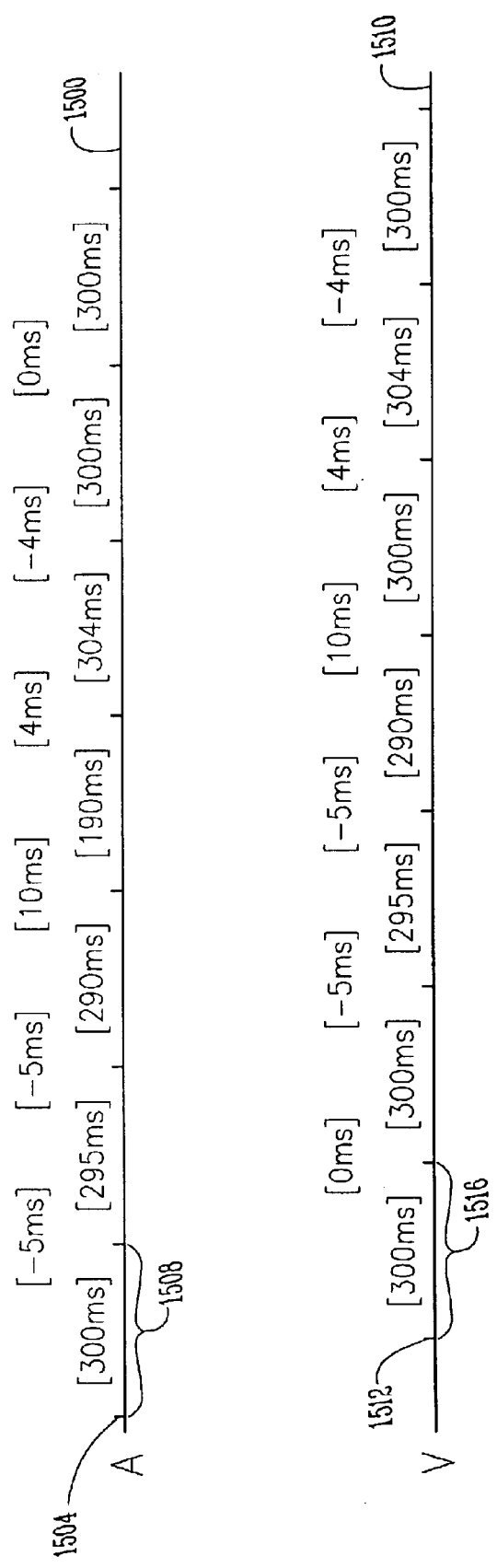
FIG. 15 is a schematic illustrating one embodiment of pairing of atrial and ventricular cycle lengths.

Referring to FIG. 15, there is shown one embodiment of cardiac cycle lengths useful in determining correlation coefficients. At 1500, there is shown atrial cycle lengths, where 1504 indicates the occurrence of atrial contractions and the atrial cycle lengths are shown at 1508. At 1510, there is shown ventricular cycle lengths, where 1512 indicates the occurrence of ventricular contraction and the ventricular cycle lengths are shown at 1516.

In one embodiment, using the atrial cycle lengths 1508 the atrial timing difference values between pairs of successive atrial cycle lengths are −5 ms, −5 ms, 100 ms, 114 ms, −4 ms, and 0 ms. Similarly, using the ventricular cycle lengths 1516 the ventricular timing difference values between pairs of successive ventricular cycle lengths are 0 ms, −5 ms, −5 ms, 10 ms, 4 ms, and −4 ms. Prior to paring the atrial timing difference values with the ventricular timing difference values in the antegrade and retrograde directions, the atrial timing difference values are assigned an atrial integer value and the ventricular timing difference values are assigned a ventricular integer value.

In one embodiment, assigning each of the atrial timing difference values an atrial integer value is done as a function of the magnitude of each of the atrial timing difference values. In addition, assigning each of the ventricular timing difference values an ventricular integer value is also done as a function of the magnitude of each of the ventricular timing difference values. As previously discussed, when the magnitude of the ventricular timing difference value and/or the magnitude of the atrial timing difference value is approximately zero, the difference is represented by a zero (0). When the magnitude of the ventricular timing difference value and/or the magnitude of the atrial timing difference value exceeds 2 ms, the difference is represented by a +1 or a −1. Finally, when the magnitude of the timing difference value and/or the magnitude of the atrial timing difference value exceeds 10 ms, the difference is represented by a +2 or a −2.

In the present embodiment, the atrial timing difference values [−5 ms, −5 ms, 100 ms, 114 ms, −4 ms, 0 ms] are each assigned an atrial integer value [−1, −1, 2, 2, −1, 0]. Likewise, the ventricular timing difference values [0 ms, −5 ms, −5 ms, 10 ms, 4 ms, −4 ms] are each assigned a ventricular integer value [0, −1, −1, 2, 1, −1]. An antegrade correlation coefficient is then determined from the atrial integer values paired with the ventricular integer values in the antegrade direction, and a retrograde correlation coefficient is determined from the atrial integer values paired with the ventricular integer values in the retrograde direction. The tachycardia event is then classified as occurring in either an antegrade direction or in a retrograde direction depending upon which correlation coefficient has the larger value as previously discussed.

In an additional embodiment, atrial and ventricular cycle lengths sensed during a tachycardia episode can often time change during the course of the tachycardiac episode. For example, the atrial and ventricular cycle lengths can become increasingly smaller as the tachycardia episode progresses. In this situation, the heart rate of the patient increases. When the cardiac cycle lengths in both the atria and ventricle steadily decrease, a meaningful association between the cycle lengths can not always be ascertained.

In one embodiment, to restore a portion of this association an estimated value of a change in the series of the atrial cycle lengths and a series of the ventricular cycle lengths can be determined. In one embodiment, this can be predicted by calculating an atrial trend value in the atrial cycle lengths by fitting a first curve to a series of atrial cycle lengths. In one embodiment, the series of atrial cycle lengths are determined from the sensed atrial contractions. Additionally, a ventricular trend value is also calculated for the ventricular cycle lengths by fitting a second curve to a series of ventricular cycle lengths. In one embodiment, the series of ventricular cycle lengths are determined from the sensed ventricular contractions. In one embodiment, the first and second curves can be fit by applying linear regression, parabolic regression, or cubic regression. In one embodiment, the cardiac data analyzing circuit is adapted to perform these functions.

Once the first and second curves have been fit, the atrial trend value and the ventricular trend value is determined from the slope of the first and second curve, respectively. Thus, the atrial and ventricular trend values are determined from the slope of the rate of change in the atrial and ventricular cycle lengths, subtracting the atrial trend value from each atrial cycle length. The atrial trend value and the ventricular trend value are then subtracted from the atrial cycle lengths and the ventricular cycle lengths, respectively, as they are determined. Correlation coefficients are then determined using the processed cycle lengths and used to classify the ventricular tachyarrhythmia.

We claim:

1. A system for determining a direction of conduction of an arrhythmia episode between a first cardiac region and a second cardiac region, the system comprising:

a first electrode to sense a first signal indicative of first contractions in the first cardiac region;

a second electrode to sense a second signal indicative of second contractions in the second cardiac region;

a first contraction detector circuit, coupled to the first electrode, to detect the first contractions;

a second contraction detector circuit, coupled to the second electrode, to detect the second contractions;

a cardiac data analyzing circuit coupled to the first contraction detector circuit and the second contraction detector circuit, the cardiac data analyzing circuit adapted to:

determine first cycle lengths each being a time interval between two successively sensed first contractions;

determine second cycle lengths each being a time interval between two successively sensed second contractions; and analyze the first and second contractions to determine an occurrence of an arrhythmia episode having a one-to-one association of the first contractions to the second contractions;

a cycle length pairing circuit coupled to the cardiac data analyzing circuit, the cycle length pairing circuit adapted to pair the first cycle lengths with the second cycle lengths in first and second directions during the arrhythmia episode having the one-to-one association of the first contractions to the second contractions, the first direction corresponding to a direction of conduction of the arrhythmia episode from the first cardiac region to the second cardiac region, the second direction corresponding to a direction of conduction of the arrhythmia episode from the second cardiac region to the first cardiac region; and a processor coupled to the cycle length pairing circuit, the processor adapted to:

determine correlation coefficients each for the first cycle lengths paired with the second cycle lengths in one of the first and second directions; and determine the direction of the conduction of the arrhythmia episode based on the correlation coefficients.

2. The system of claim 1, wherein the first electrode is an atrial electrode, and the second electrode is a ventricular electrode.

3. The system of claim 2, further comprising a pacing output circuit coupled to the atrial electrode.

4. The system of claim 2, further comprising a pacing output circuit coupled to the ventricular electrode.

5. The system of claim 1, wherein the cycle length pairing circuit is adapted to:

pair the first cycle lengths with the second cycle lengths in the first direction, where for each of the paired first and second cycle lengths, the first cycle lengths starts before the second cycle length starts; and pair the first cycle lengths with the second cycle lengths in the second direction, where for each of the paired first and second cycle lengths, the first cycle lengths starts after the second cycle length starts.

6. The system of claim 5, wherein the processor is adapted to:

determine a first correlation coefficient for the first cycle lengths paired with the second cycle lengths in the first direction;

determine a second correlation coefficient for the first cycle lengths paired with the second cycle lengths in the second direction; and determining the direction of the conduction of the arrhythmia episode based on the first and second correlation coefficients.

7. The system of claim 1, wherein the cycle length pairing circuit is adapted to:

pair the first cycle lengths with the second cycle lengths in the first direction, where for each of the paired first and second cycle lengths, the first cycle length ends before the second cycle length starts; and pair the first cycle lengths with the second cycle lengths in the second direction, where for each of the paired first and second cycle lengths, the first cycle length starts after the second cycle length ends.

8. The system of claim 7, wherein the processor is adapted to:

determine a first correlation coefficient for the first cycle lengths paired with the second cycle lengths in the first direction;

determine a second correlation coefficient for the first cycle lengths paired with the second cycle lengths in the second direction; and determine the direction of the conduction of the arrhythmia episode based on the first and second correlation coefficients.

9. A method for determining a direction of conduction of an arrhythmia episode between a first cardiac region and a second cardiac region, the method comprising:

sensing first contractions from the first cardiac region and second contractions from the second cardiac region;

determining first cycle lengths from the first contractions;

determining second cycle lengths from the second contractions;

analyzing the first and second contractions for an occurrence of an arrhythmia episode that has a one-to-one association of the first contractions to the second contractions;

analyzing correlations between the first cycle lengths and the second cycle lengths during the arrhythmia episode; and determining the direction of the conduction of the arrhythmia episode based on the correlations.

10. The method of claim 9, wherein the first cardiac region comprises an atrial region, and the second cardiac region comprises a ventricular region.

11. The method of claim 10, further comprising delivering pacing pulses to the atrial region during the arrhythmia episode.

12. The method of claim 10, further comprising delivering pacing pulses to the ventricular region during the arrhythmia episode.

13. The method of claim 9, wherein analyzing the correlations between the first cycle lengths and the second cycle lengths during the arrhythmia episode comprising:

pairing the first cycle lengths with the second cycle lengths in a first direction, where for each of the paired first and second cycle lengths, the first cycle lengths starts before the second cycle length starts;

pairing the first cycle lengths with the second cycle lengths in a second direction, where for each of the paired first and second cycle lengths, the first cycle lengths starts after the second cycle length starts;

determining a first correlation coefficient for the first cycle lengths paired with the second cycle lengths in the first direction; and determining a second correlation coefficient for the first cycle lengths paired with the second cycle lengths in the second direction.

14. The method of claim 13, wherein determining the direction of the conduction of the arrhythmia episode based on the correlations comprises determining the direction of the conduction of the arrhythmia episode based on the first and second correlation coefficients.

15. The method of claim 14, wherein determining the direction of the conduction of the arrhythmia episode comprises determining that the arrhythmia episode is conducted from the first cardiac region to the second cardiac region when the first correlation coefficient is greater than the second correlation coefficient.

16. The method of claim 14, wherein determining the direction of the conduction of the arrhythmia episode comprises determining that the arrhythmia episode is conducted from the second cardiac region to the first cardiac region when the second correlation coefficient is greater than the first correlation coefficient.

17. The method of claim 14, comprising determining the first correlation coefficient and the second correlation coefficient each from a predetermined sample size of between 10 to 1000 paired first cycle lengths and second cycle lengths.

18. The method of claim 14, including using a Fisher Z transformation to determine whether the first correlation coefficient and the second correlation coefficient are statistically different.

19. The method of claim 9, wherein analyzing the correlations between the first cycle lengths and the second cycle lengths during the arrhythmia episode comprising:

pairing the first cycle lengths with the second cycle lengths in a first direction, where for each of the paired first and second cycle lengths, the first cycle length ends before the second cycle length starts;

pairing the first cycle lengths with the second cycle lengths in a second direction, where for each of the paired first and second cycle lengths, the first cycle length starts after the second cycle length ends;

determining a first correlation coefficient the first cycle lengths paired with the second cycle lengths in the first direction; and determining a second correlation coefficient the first cycle lengths paired with the second cycle lengths in the second direction.

20. The method of claim 19, wherein determining the direction of the conduction of the arrhythmia episode based on the correlations comprises determining the direction of the conduction of the arrhythmia episode based on the first and second correlation coefficients.

21. The method of claim 20, wherein determining the direction of the conduction of the arrhythmia episode comprises determining that the arrhythmia episode is conducted from the first cardiac region to the second cardiac region when the first correlation coefficient is greater than the second correlation coefficient.

22. The method of claim 20, wherein determining the direction of the conduction of the arrhythmia episode comprises determining that the arrhythmia episode is conducted from the second cardiac region to the first cardiac region when the second correlation coefficient is greater than the first correlation coefficient.

23. The method of claim 20, comprising determining the first correlation coefficient and the second correlation coefficient each from a predetermined sample size of between 10 to 1000 paired first cycle lengths and second cycle lengths.

24. The method of claim 20, including using a Fisher Z transformation to determine whether the first correlation coefficient and the second correlation coefficient are statistically different.

25. A method, comprising:

sensing atrial contractions and ventricular contractions;

determining atrial cycle lengths each being a time interval between a sensed first atrial contraction and a successively sensed second atrial contraction;

determining ventricular cycle lengths each being a time interval between a sensed first ventricular contraction and a successively sensed second ventricular contraction;

analyzing the atrial contractions and ventricular contractions for an occurrence of a tachycardia episode having an one-to-one association of atrial contractions to ventricular contractions;

determining atrial timing difference values each between a first atrial cycle length and a succeeding second atrial cycle length during the tachycardia episode;

determining ventricular timing difference values each between a first ventricular cycle length and a succeeding second ventricular cycle length during the tachycardia episode; and analyzing correlations between the atrial timing difference and the ventricular timing difference during the tachycardia episode; and classifying the tachycardia episode based on the correlations.

26. The method of claim 25, wherein analyzing the correlations comprises:

pairing the atrial timing difference values with the ventricular timing difference values in an antegrade direction, where for each of the paired atrial and ventricular time difference values, the first atrial cycle length starts before the first ventricular cycle length starts;

pairing the atrial timing difference values with the ventricular timing difference values in a retrograde direction, where for each of the paired atrial and ventricular time difference values, the first atrial cycle length starts after the first ventricular cycle length starts;

determining an antegrade correlation coefficient for the atrial timing difference values paired with the ventricular timing difference values in the antegrade direction; and determining a retrograde correlation coefficient for the atrial timing difference values paired with the ventricular timing difference values in the retrograde direction, and wherein classifying the tachycardia episode comprises classifying the tachycardia episode based on the antegrade correlation coefficient and the retrograde correlation coefficient.

27. The method of claim 26, wherein classifying the tachycardia episode comprises classifying the tachycardia episode as occurring in the antegrade direction if the antegrade correlation coefficient is greater than the retrograde correlation coefficient.

28. The method of claim 26, wherein classifying the tachycardia episode comprises classifying the tachycardia episode as occurring in the retrograde direction if the retrograde correlation coefficient is greater than the antegrade correlation coefficient.

29. The method of claim 25, wherein analyzing the corrections comprises:

pairing the atrial timing difference values with the ventricular timing difference values in a super-antegrade direction, where for each of the paired atrial and ventricular time difference values, the first atrial cycle length ends before the first ventricular cycle length starts;

pairing the atrial timing difference values with the ventricular timing difference values in a super-retrograde direction, where for each of the paired atrial and ventricular time difference values, the first atrial cycle length starts after the first ventricular cycle length ends;

determining a super-antegrade correlation coefficient for the atrial timing difference values paired with the ventricular timing difference values in the antegrade direction;

determining a super-retrograde correlation coefficient for the atrial timing difference values paired with the ventricular timing difference values in the retrograde direction, and wherein classifying the tachycardia episode comprises classifying the tachycardia episode based on the super-antegrade correlation coefficient and the super-retrograde correlation coefficient.

30. The method of claim 29, wherein classifying the tachycardia episode comprises classifying the tachycardia episode as occurring in the antegrade direction if the super-antegrade correlation coefficient is greater than the super-retrograde correlation coefficient.

31. The method of claim 29, wherein classifying the tachycardia episode comprises classifying the tachycardia episode as occurring in the retrograde direction if the super-retrograde correlation coefficient is greater than the super-antegrade correlation coefficient.

32. A system, comprising:

means for determining atrial cycle lengths each being a time interval between two successively sensed atrial contractions and determining ventricular cycle lengths each being a time interval between two successively sensed ventricular contractions;

means for detecting an occurrence of a tachycardia episode having an one-to-one association of the atrial contractions to the ventricular contractions;

means for analyzing correlations between the atrial cycle lengths and the ventricular cycle lengths during the tachycardia episode, the means for analyzing the correlations including:

means for pairing the atrial cycle lengths with the ventricular cycle lengths in an antegrade direction and pairing the atrial cycle lengths with the ventricular cycle lengths in a retrograde direction; and means for determining an antegrade correlation coefficient for the atrial cycle lengths paired with the ventricular cycle lengths in the antegrade direction and determining a retrograde correlation coefficient for the atrial cycle lengths paired with the ventricular cycle lengths in the retrograde direction.

33. The system of claim 32, further comprising means for classifying the tachycardia episode based on the antegrade correlation coefficient and the retrograde correlation coefficient.

34. The system of claim 33, further comprising means for delivering pacing pulses during the tachycardia episode.

* * * * *

UNITED STATES PATENT AND TRADEMARK OFFICE
CERTIFICATE OF CORRECTION

PATENT NO.        : 7,062,316 B2
APPLICATION NO. : 10/347725
DATED             : June 13, 2006
INVENTOR(S)       : Hsu et al.

It is certified that error appears in the above-identified patent and that said Letters Patent is hereby corrected as shown below:

on title page, in item (56), under "Foreign Patent Documents", in column 2, line 1, after "8/1981" insert - - A61N 1/36 - -.

column 24, line 23, in Claim 25, delete "an" and insert - - a - -, therefor.

column 24, line 32, in Claim 25, after "episode;" delete "and".

column 25, line 7, in Claim 29, delete "corrections" and insert - - correlations - -, therefor.

column 26, line 12, in Claim 32, delete "an" and insert - - a - -, therefor.

Signed and Sealed this

Fifth Day of September, 2006

JON W. DUDAS
*Director of the United States Patent and Trademark Office*